US012667379B2

(12) United States Patent
Takikawa

(10) Patent No.: US 12,667,379 B2
(45) Date of Patent: Jun. 30, 2026

(54) FORCEPS DEVICE

(71) Applicant: RIVERFIELD Inc., Tokyo (JP)

(72) Inventor: Kyohei Takikawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 170 days.

(21) Appl. No.: 18/773,785

(22) Filed: Jul. 16, 2024

(65) Prior Publication Data

US 2024/0366249 A1     Nov. 7, 2024

Related U.S. Application Data

(63) Continuation of application No. PCT/JP2022/001338, filed on Jan. 17, 2022.

(51) Int. Cl.
*A61B 17/29* (2006.01)
*A61B 34/00* (2016.01)

(52) U.S. Cl.
CPC .............. *A61B 17/29* (2013.01); *A61B 34/71* (2016.02); *A61B 2017/2903* (2013.01)

(58) Field of Classification Search
CPC . A61B 17/29; A61B 34/71; A61B 2017/2901; A61B 2017/2902; A61B 2017/2903; A61B 2090/035
See application file for complete search history.

(56) References Cited

U.S. PATENT DOCUMENTS 7,300,373 B2 * 11/2007 Jinno ........................ B25J 9/104
474/174
8,500,721 B2 * 8/2013 Jinno ................. A61B 17/2909
606/1

9,937,626 B2 * 4/2018 Rockrohr ................ A61B 34/30
10,624,703 B2 * 4/2020 Chaplin ........... A61B 17/00234
10,667,856 B2 * 6/2020 Felder .................... A61B 17/32
10,751,140 B2 * 8/2020 Wallace ................. A61B 34/71
10,973,600 B2 * 4/2021 Bruehwiler ........... A61B 34/71
11,045,269 B2 * 6/2021 Sachs ................. A61B 17/3417
11,484,298 B2 * 11/2022 Chaplin ................. A61B 34/71
11,576,732 B2 * 2/2023 Wentworth ...... A61B 17/00234
11,950,863 B2 * 4/2024 Chin .................. A61B 18/1445
12,390,238 B2 * 8/2025 Tadano .............. A61B 17/2804
2004/0266574 A1 * 12/2004 Jinno ..................... A61B 34/71
474/174

(Continued)

FOREIGN PATENT DOCUMENTS

CN          107928792 A      4/2018
JP          2020-73013 A     5/2020

(Continued)

OTHER PUBLICATIONS

U.S. Appl. No. 18/773,808, Kyohei Takikawa, filed Jul. 16, 2024.

(Continued)

*Primary Examiner* — Ryan J. Severson
(74) *Attorney, Agent, or Firm* — Sughrue Mion, PLLC

(57) ABSTRACT

A forceps device includes grasping portions, a support that holds the grasping portions, a first rotating shaft that turnably supports the support, a base member that holds the first rotating shaft, first wires that transmit driving forces to move the grasping portions, second wires that transmit a driving force to turn the support about the first rotating shaft, and a stopper that prevents the support from touching the first wires.

20 Claims, 20 Drawing Sheets

(56)                References Cited

U.S. PATENT DOCUMENTS

| | | | |
|---|---|---|---|
| 2010/0228283 A1* | 9/2010 | Jinno | A61B 34/70 606/205 |
| 2016/0303743 A1 | 10/2016 | Rockrohr | |
| 2017/0165017 A1* | 6/2017 | Chaplin | A61B 17/00234 |
| 2017/0252096 A1* | 9/2017 | Felder | A61B 18/1445 |
| 2018/0311000 A1 | 11/2018 | Ishihara et al. | |
| 2019/0099231 A1* | 4/2019 | Bruehwiler | A61B 10/04 |
| 2019/0142531 A1* | 5/2019 | Wentworth | A61B 17/00234 606/130 |
| 2019/0374297 A1* | 12/2019 | Wallace | A61B 34/30 |
| 2020/0093468 A1* | 3/2020 | Chaplin | A61B 34/30 |
| 2020/0170728 A1* | 6/2020 | Ishihara | A61B 17/2812 |
| 2020/0170729 A1* | 6/2020 | Ishihara | A61B 34/71 |
| 2020/0197112 A1 | 6/2020 | Chin et al. | |
| 2020/0246093 A1* | 8/2020 | Sachs | A61B 17/3417 |
| 2021/0196416 A1* | 7/2021 | Betsugi | A61B 34/35 |
| 2021/0401445 A1 | 12/2021 | Kapadia | |
| 2022/0175408 A1 | 6/2022 | Lee et al. | |
| 2022/0313296 A1 | 10/2022 | Tadano et al. | |
| 2023/0210546 A1* | 7/2023 | Takikawa | A61B 34/30 606/205 |
| 2023/0310106 A1* | 10/2023 | Takikawa | A61B 17/29 606/205 |
| 2024/0366248 A1* | 11/2024 | Takikawa | A61B 17/2812 |
| 2024/0366249 A1* | 11/2024 | Takikawa | A61B 34/71 |
| 2024/0366250 A1* | 11/2024 | Takikawa | A61B 34/30 |

FOREIGN PATENT DOCUMENTS

| | | |
|---|---|---|
| WO | 2015/088647 A1 | 6/2015 |
| WO | 2020/131529 A1 | 6/2020 |
| WO | 2021/130945 A1 | 7/2021 |

OTHER PUBLICATIONS

U.S. Appl. No. 18/773,791, Kyohei Takikawa, filed Jul. 16, 2024.
Communication dated Oct. 2, 2025 from the United States Patent and Trademark Office in U.S. Appl. No. 18/773,808.
Communication dated Oct. 2, 2025 from the United States Patent and Trademark Office in U.S. Appl. No. 18/773,791.

* cited by examiner

10

10

14b

14b

15

16

42

14

14

14b

14b

42

14

10

82

FORCEPS DEVICE

CROSS-REFERENCE TO RELATED APPLICATION

This Application is a Continuation Application of International Application No. PCT/JP2022/001338, filed on Jan. 17, 2022 in the Japan Patent Office, the contents of which being herein incorporated by reference in its entirety.

BACKGROUND

The present disclosure relates to a forceps device used for a manipulator of a surgical robot.

Medical treatments using robots (manipulators) have recently been proposed in order to reduce the burden on operators and save manpower in medical facilities. In the field of surgery, proposals have been made for surgical manipulator systems for operators to treat patients by operating remotely-controllable surgical manipulators.

Various surgical tools may be attached to leading ends of surgical manipulators. Known surgical tools include, for example, forceps for grasping human tissue during surgery.

SUMMARY

It is an aspect to provide a novel technology for improving the durability of wires of the forceps device.

According to an aspect of one or more embodiments, there is provided a forceps device comprising a grasping part; a support that holds the grasping part; a first rotating shaft that turnably supports the support; a base member that holds the first rotating shaft; a plurality of grasping-portion wires that transmit driving forces to move the grasping part; a support wire that transmits a driving force to turn the support about the first rotating shaft; and a turning restricting mechanism that restricts turning of the support so that the support that is turned does not touch the plurality of grasping-portion wires.

According to another aspect of one or more embodiments, there is provided a forceps device comprising a grasping part; a support that holds the grasping part; a first rotating shaft that turnably supports the support; a base member that holds the first rotating shaft; a plurality of grasping-portion wires that transmit driving forces to move the grasping part; a plurality of support wires that transmit a driving force to turn the support about the first rotating shaft; and a stopper that prevents the support from touching the plurality of grasping-portion wires.

According to yet another aspect of one or more embodiments, there is provided a forceps device comprising a plurality of grasping portions; a support that holds the plurality of grasping portions; a first rotating shaft that turnably supports the support; a base member that holds the first rotating shaft; a plurality of first wires that transmit driving forces to move the plurality of grasping portions; a plurality of second wires that transmit a driving force to turn the support about the first rotating shaft; and a stopper that prevents the support from touching the plurality of first wires.

BRIEF DESCRIPTION OF DRAWINGS

The above and other aspects will be described more fully below with reference to the drawings, in which.

DETAILED DESCRIPTION

Figure 1:
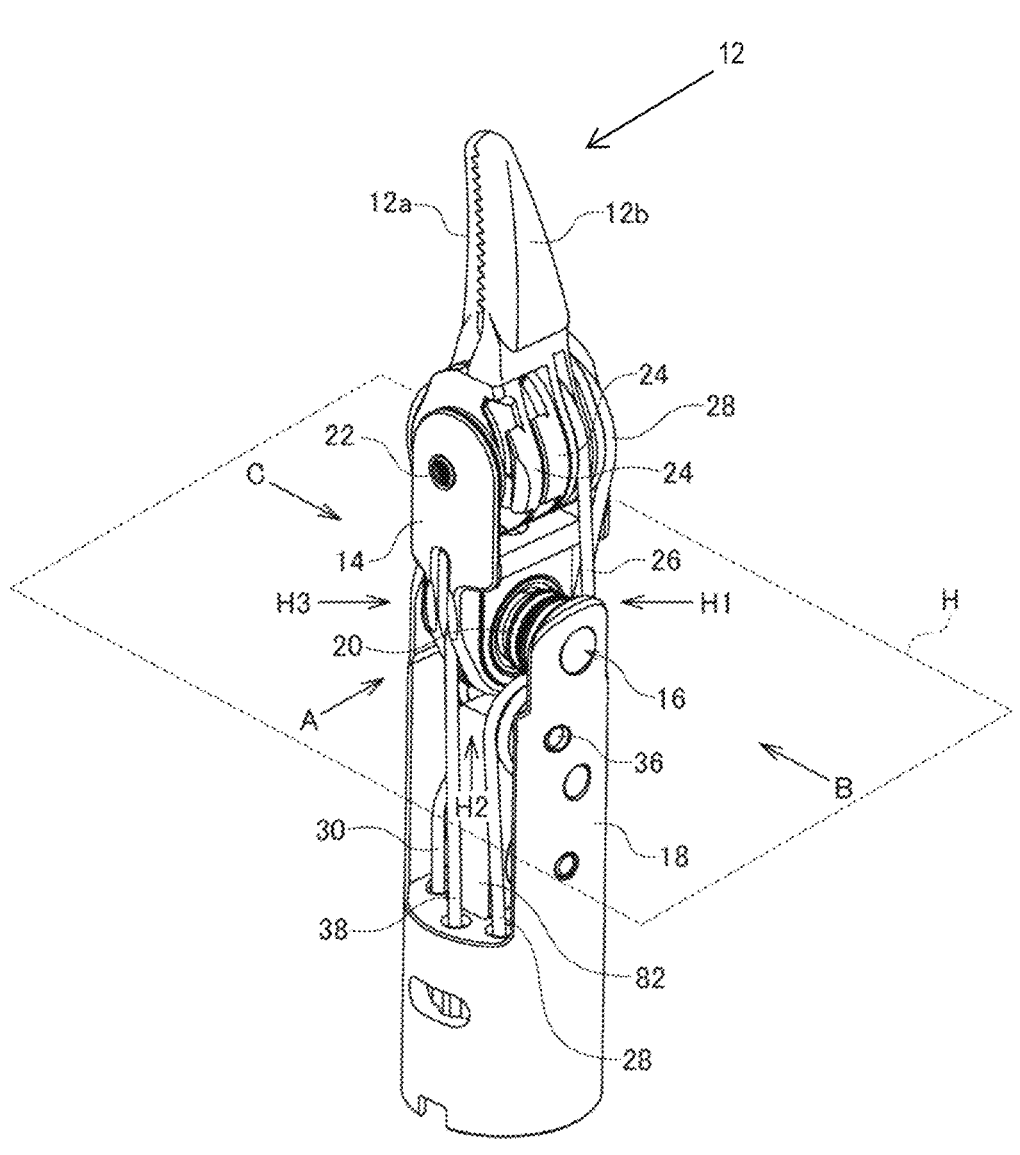
FIG. 1 is a perspective view of a forceps device according to an embodiment.

In the related art, a forceps device may include a first rotating shaft that turnably supports a support holding a grasping part, a base member that holds the first rotating shaft, a plurality of guide pulleys arranged coaxially with the first rotating shaft, and a plurality of grasping-portion wires that transmit driving forces to move the grasping part, the grasping-portion wires running between the plurality of guide pulleys and the grasping part without other pulleys.

When the support of the forceps device according to the related art is greatly turned about the first rotating shaft, there is a disadvantage in that part of the support may touch a grasping-portion wire. If the grasping-portion wire moves in this state, the durability of the grasping-portion wire may be lowered owing to friction against the support.

Various embodiments have been made in view of the aforementioned disadvantages, and it is an aspect to provide a novel technology for improving the durability of wires of the forceps device.

To address the aforementioned disadvantages, a forceps device according to an embodiment may include a grasping part; a support that holds the grasping part; a first rotating shaft that turnably supports the support; a base member that holds the first rotating shaft; a plurality of grasping-portion wires that transmit driving forces to move the grasping part; a support wire that transmits a driving force to turn the support about the first rotating shaft; and a turning restricting mechanism that restricts turning of the support so that the turning support does not touch the grasping-portion wires.

According to this configuration and operation, the support is prevented from touching the grasping-portion wires, and the durability of the wires is therefore improved.

In some embodiments, the turning restricting mechanism may include a stopper having a face with which part of the turning support comes into contact. This configuration enables more reliable prevention of contact between the support and the grasping-portion wires.

In some embodiments, the stopper may be a block-like member having a flat face facing the support, the flat face serving as the face with which the turning support comes into contact. As a result, the turning restricting mechanism can be achieved with a simple part.

In some embodiments, the support may have an outer edge at which a flat contact face is formed, the flat contact face being inclined with respect to a central axis of the base member at a neutral position at which the support is not turned to left or right, the support coming into contact with the stopper when a turning angle from the neutral position becomes a contact angle $\beta$ ($\alpha<\beta$) beyond angles $\alpha$ in a control range angle. This configuration and operation prevents the support from turning at angles larger than the contact angle $\beta$ while permitting turning at the angles $\alpha$ in the predetermined control range, which prevents hindrance to turning control of the support by the stopper.

In some embodiments, the contact angle $\beta$ may be 70° or larger. This configuration enables control of the turning of the support at least up to 70°.

In some embodiments, the stopper may be positioned relative to the base member. As a result, both the support and the stopper are at predetermined positions relative to the base member, which improves the accuracy of relative positions of the support and the stopper.

In some embodiments, the stopper may be located in a region surrounded by the plurality of grasping-portion wires and support wires. Thus, the region surrounded by the plurality of wires may be occupied by the stopper, which prevents foreign substances from staying inside the forceps device (in a region surrounded by the wires) as compared with a case where no stopper is provided.

In some embodiments, the base member may include a pair of arms that hold respective ends of the first rotating shaft. The pair of arms may hold a positioning pin extending through the stopper. As a result, the stopper can be accurately positioned in the axial direction of the base member. Furthermore, because the pair of arms holds the positioning pin, the strength of the arms is increased.

In some embodiments, the base member may include a partition part at a base part of the arms, the partition part may have a plurality of projections to be used for positioning of the stopper, and the plurality of projections may be configured to position the stopper in a direction intersecting a central axis of the base member. As a result, the stopper can be accurately positioned in the direction intersecting the axial direction of the base member.

In some embodiments, a method, a device, a system, and the like consistent with the above embodiments may also be provided to address the above disadvantages.

According to the various embodiments, the durability of wires of the forceps device may be improved.

Various embodiments will now be described with reference to the drawings. Components, members, and processes that are the same as or equivalent to each other illustrated in the drawings are represented by the same reference numerals, and redundant explanation will not be repeated for conciseness. The various embodiments are not limited to those described herein, but rather are examples, and in the various embodiments, it is to be understood that any feature or any combination of features described are not necessarily essential to the invention.

[Forceps Device]

FIG. 1 is a perspective view of a forceps device according to an embodiment.

Figure 2:
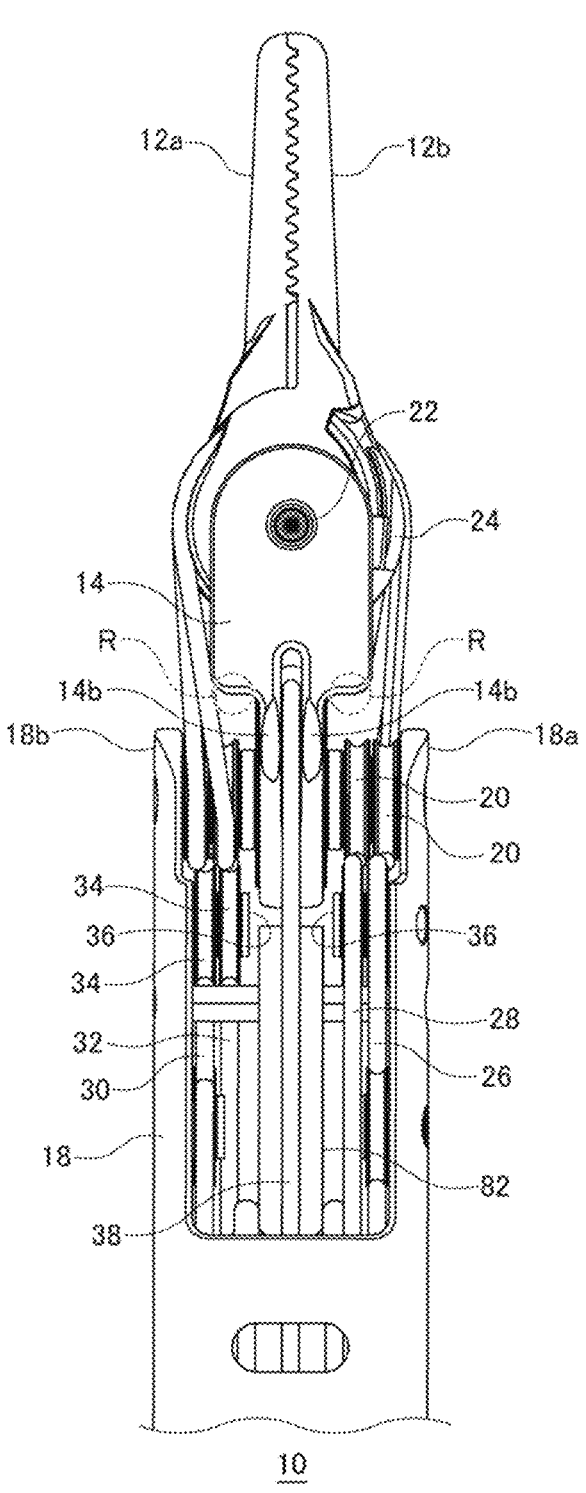
FIG. 2 is a front view of the forceps device of FIG. 1 as viewed in a direction A.
Figure 3:
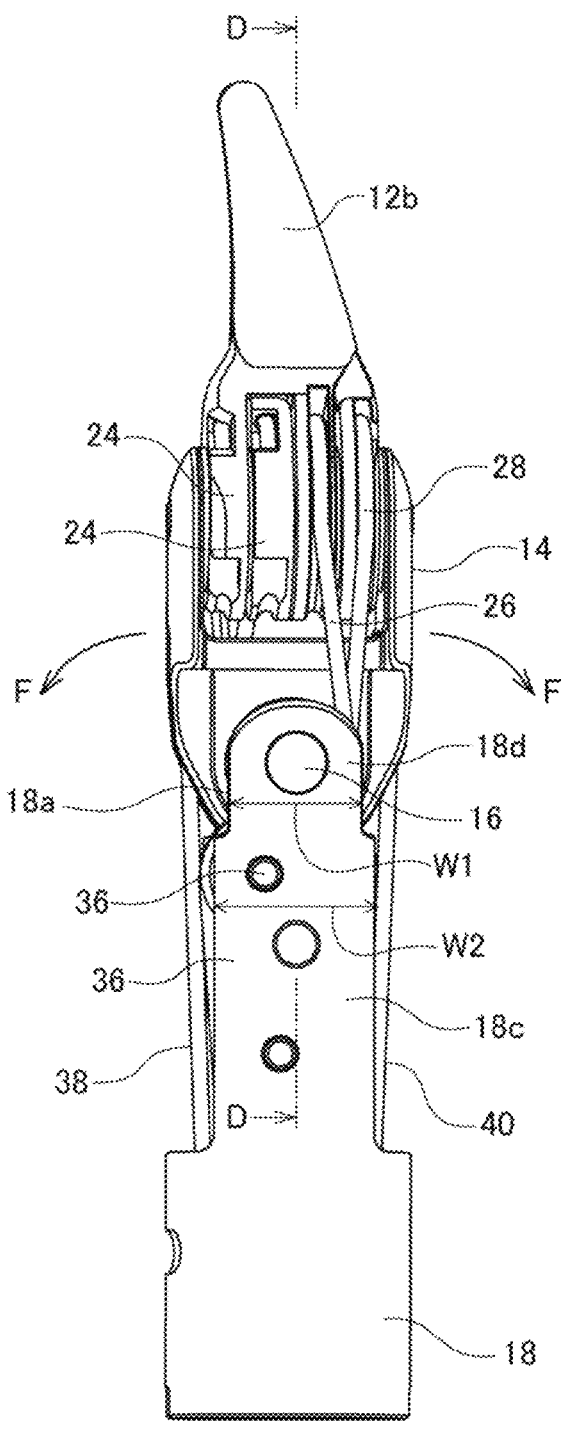
FIG. 3 is a side view of the forceps device of FIG. 1 as viewed in a direction B.
Figure 4:
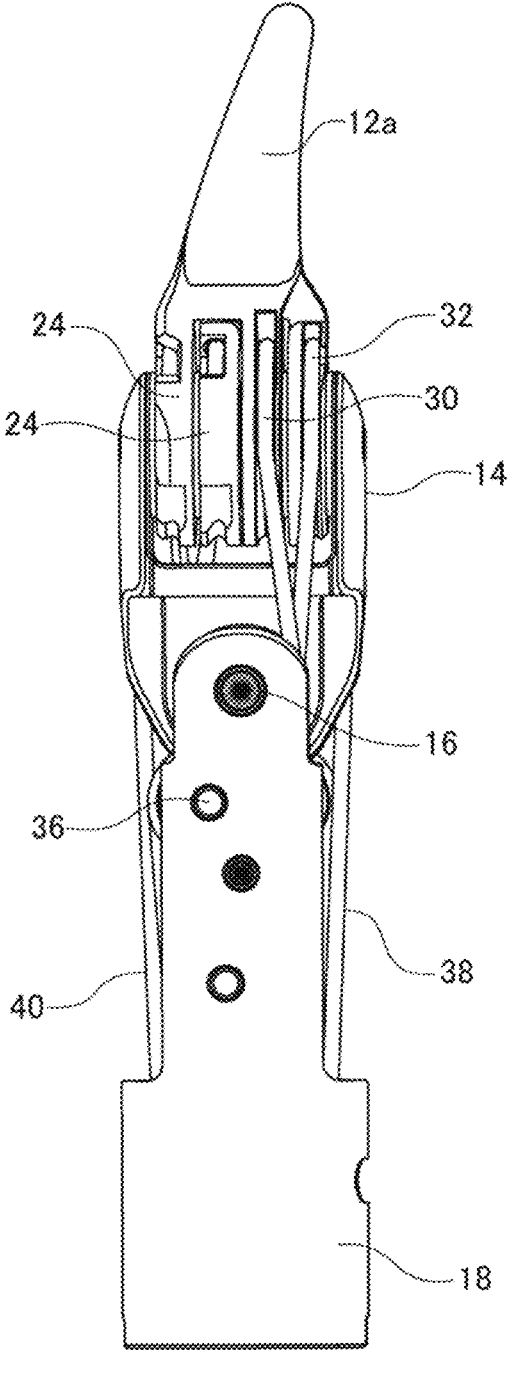
FIG. 4 is a side view of the forceps device of FIG. 1 as viewed in a direction C.

FIG. 2 is a front view of the forceps device of FIG. 1 as viewed in a direction A. FIG. 3 is a side view of the forceps device of FIG. 1 as viewed in a direction B. FIG. 4 is a side view of the forceps device of FIG. 1 as viewed in a direction C.

The forceps device 10 illustrated in the drawings includes a pair of grasping portions 12a and 12b (collectively a grasping part 12), a support 14 that holds the pair of grasping portions 12a and 12b, a first rotating shaft 16 that turnably supports the support 14, a base member 18 that holds the first rotating shaft 16, four guide pulleys 20 arranged coaxially with the first rotating shaft 16, a second rotating shaft 22 that turnably supports the pair of grasping portions 12a and 12b and is held by the support 14, four jaw pulleys 24 supported coaxially with the second rotating shaft 22, four wires 26, 28, 30 and 32 running over the four guide pulleys 20 and the four jaw pulleys 24, and support wires 38 and 40 for turning the support 14 about the first rotating shaft 16.

[Guide Pulleys 20]

Figure 5:
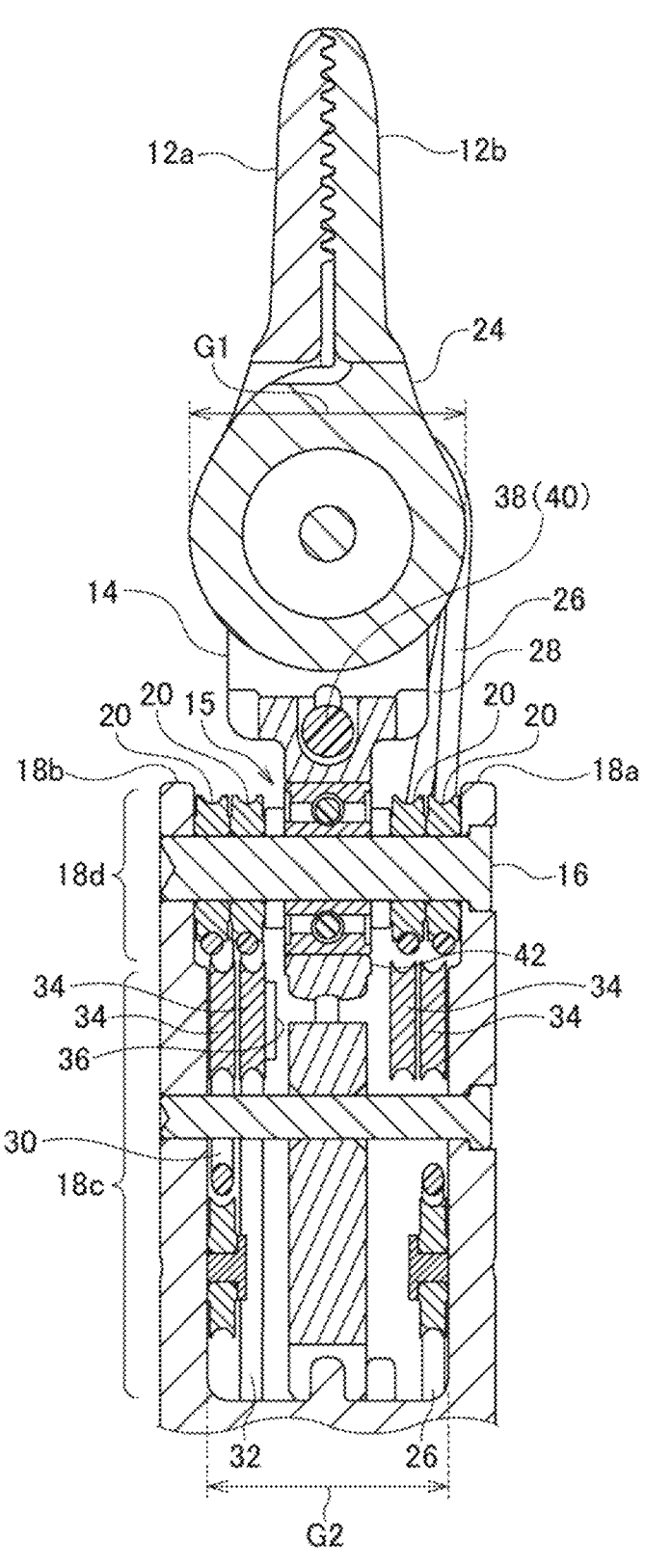
FIG. 5 is a cross-sectional view of the forceps device illustrated in FIG. 3 along D-D.

FIG. 5 is a cross-sectional view of the forceps device 10 illustrated in FIG. 3 along D-D. As illustrated in FIG. 5, the guide pulleys 20 are rotatably supported by the first rotating shaft 16 inserted in a bearing 15 mounted on the support 14. As illustrated in FIG. 5, the guide pulleys 20 are arranged in such a manner that two guide pulleys 20 adjacent to each other are present on respective sides with respect to the support 14.

[Base Member]

Next, the base member 18 will be described. As illustrated in FIG. 2 and FIG. 5, the base member 18 includes a pair of arms 18a and 18b that hold respective ends of the first rotating shaft 16, and third rotating shafts 36 that are held by the pair of arms 18a and 18b, respectively, and rotatably support four guide pulleys 34 located upstream of the guide pulleys 20. Note that a third rotating shaft 36 is provided on each of the pair of arms 18a and 18b. In some embodiments, the two rotating shafts 36 are arranged with their axial directions being parallel to each other but not being aligned with each other.

The arms 18a and 18b each have a base part 18c holding the third rotating shaft 36, and a distal end part 18d that holds the first rotating shaft 16 and that is thinner than the base part 18c. In other words, the distance between the distal end parts 18d is larger than the distance between the base parts 18c. Thus, as illustrated in FIG. 3, even when the wires 26 and 28 having the fleet angles are bent together with the support 14 around the first rotating shaft 16 (in the direction of an arrow F in FIG. 3), the wires 26 and 28 are less likely to interfere with the arms 18a and 18b.

Furthermore, the circumferential width W1 of the distal end part 18d of the arm 18a (the arm 18b) is smaller than the circumferential width W2 of the base part 18c thereof. Thus, a U-shaped recess is formed at the distal end part 18d at which interference with a wire may be addressed, and the circumferential width of the distal end part 18*d* is made larger than the circumferential width of the base part 18*c*, which minimizes deterioration of the stiffness of the arm.

In some embodiments, as illustrated in FIG. 5, the jaw pulleys 24 have an outer diameter G1, which is larger than the distance between the base parts 18*c* of the pair of arms 18*a* and 18*b*. Thus, in the forceps device 10, the jaw pulleys 24 having a large outer diameter relative to the inner diameter of the cylindrical base member 18 may be used.

[Support]

Figure 6:
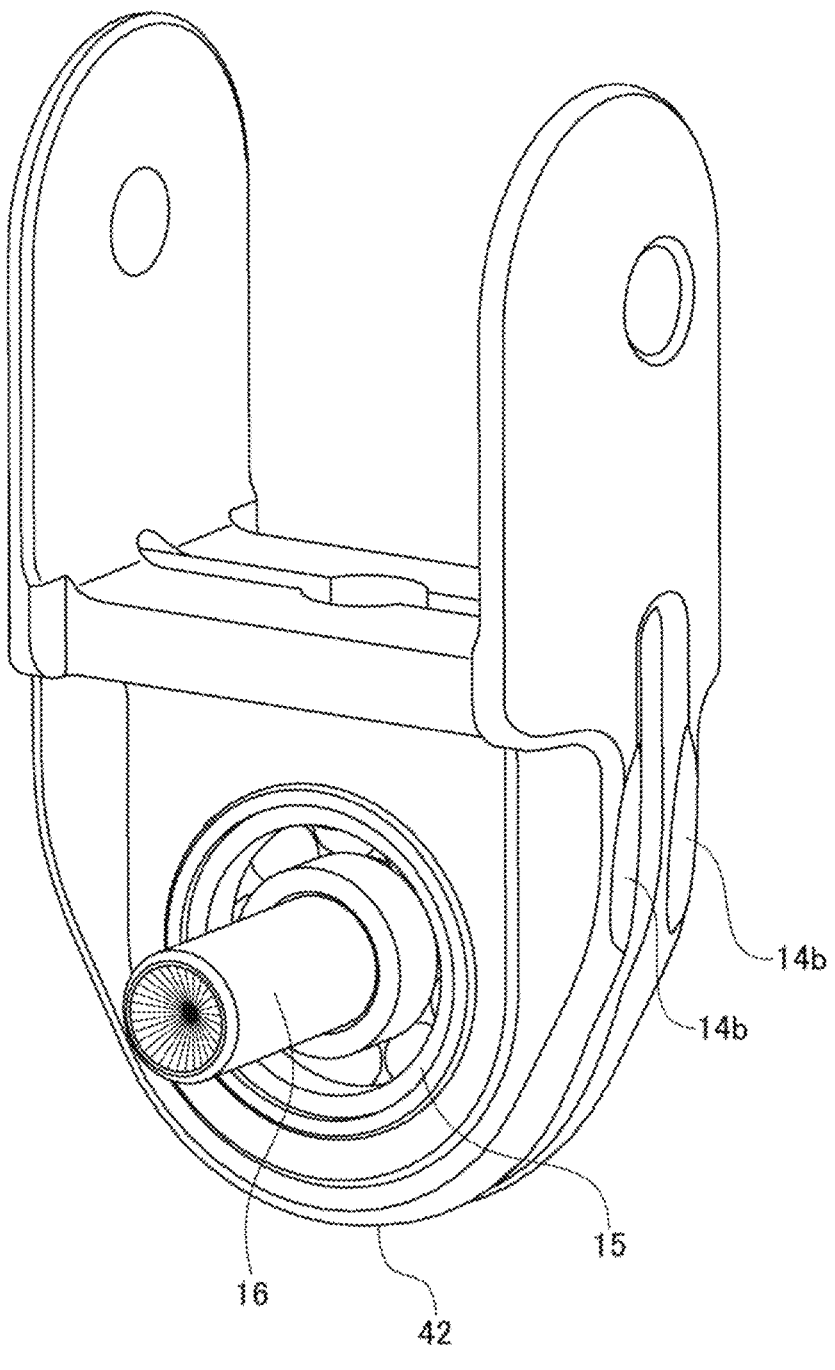
FIG. 6 is a perspective view of a support according to an embodiment.
Figure 7:
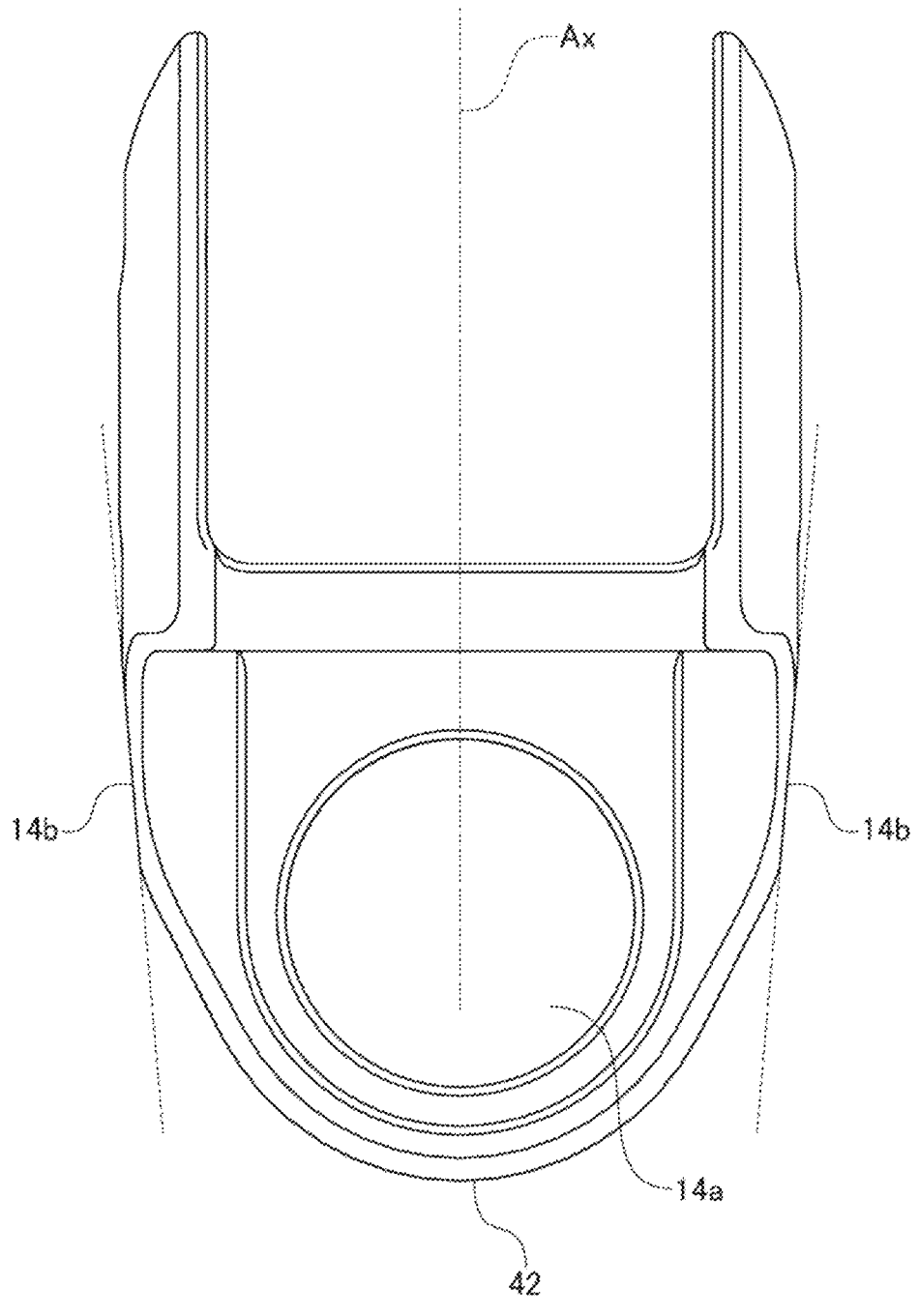
FIG. 7 is a front view of the support according to an embodiment.
Figure 8:
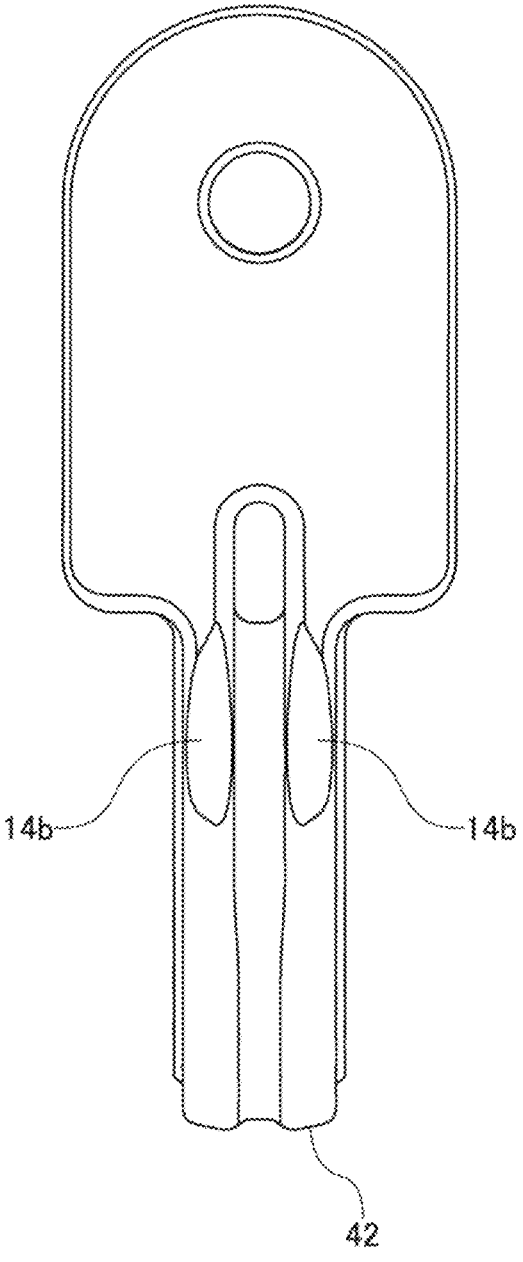
FIG. 8 is a side view of the support according to an embodiment.

FIG. 6 is a perspective view of a support according to an embodiment. FIG. 7 is a front view of the support. FIG. 8 is a side view of the support. As illustrated in FIG. 5, the forceps device 10 includes the pair of grasping portions 12*a* and 12*b*, the support 14 that holds the pair of grasping portions 12*a* and 12*b*, the first rotating shaft 16 that turnably supports the support 14, the base member 18 that holds the first rotating shaft 16, and a plurality of guide pulleys 20 arranged coaxially with the first rotating shaft 16.

As illustrated in FIG. 7, the support 14 has a circular through-hole 14*a* in which the bearing 15, which is a shaft bearing, is mounted. In some embodiments, as illustrated in FIG. 6, the first rotating shaft 16, which rotatably supports the support 14, is inserted into the bearing 15 mounted on the support 14. The guide pulleys 20 are rotatably supported by the outer circumference of the first rotating shaft 16. Note that each rotating shaft is not limited to a shaft that rotates by itself, but may be any shaft that is the center of rotation of a member supported thereby, and may be a shaft fixed to another member.

In the forceps device 10 having such a structure, the support 14 in a state in which a plurality of guide pulleys 20 are supported by the outer circumference of the first rotating shaft 16 is held by the base member 18 with the first rotating shaft 16 therebetween. This configuration facilitates improvement in the easiness of assembly as compared with a case where the support 14 is held directly by the base member 18.

In some embodiments, the base member 18 has the pair of arms 18*a* and 18*b* facing each other. The first rotating shaft 16 is firmly fixed in such a manner that the axial ends thereof are press-fitted to the pair of arms 18*a* and 18*b*. As a result, because the distal ends of the pair of arms 18*a* and 18*b*, which can be free ends, are fixed by the rotating shaft, the stiffness of the whole base member 18 increases.

Each of the wires 26, 28, 30 and 32 transmits a driving force to the grasping portion 12*a* or the grasping portion 12*b* to move the grasping portion 12*a* or the grasping portion 12*b*. Specifically, the wire 26 and the wire 32 run over the jaw pulleys 24 for the grasping portion 12*b*, and the grasping portion 12*b* moves in an opening direction when the wire 26 is pulled and moves in a closing direction when the wire 32 is pulled. The wire 28 and the wire 30 run over the jaw pulleys 24 for the grasping portion 12*a*, and the grasping portion 12*a* moves in a closing direction when the wire 28 is pulled and moves in an opening direction when the wire 30 is pulled.

In some embodiments, each of the four guide pulleys 20 has a corresponding one of the wires 26, 28, 30 and 32 placed thereover. As illustrated in FIG. 2, each of the wires 26, 28, 30 and 32 passes between the corresponding ones of the guide pulleys 20 and guide pulleys 34 and runs over the corresponding one of the guide pulleys 20 from a lower side thereof (a side opposite the grasping portion 12*a* or 12*b* with respect to the first rotating shaft 16).

A support pulley 42, over which the wires 38 and 40 for transmitting a driving force for turning the support about the first rotating shaft 16 run, is formed integrally with part of the support 14. The support pulley 42 is arranged coaxially with the first rotating shaft 16. Thus, when one of the wires 38 and 40 is pulled to turn the support 14, the tension of the wire 38 or 40 running over the support pulley 42 presses the support 14 toward the first rotating shaft 16. A normal force received by the support 14 from the first rotating shaft 16 is thus generated, which contributes to an increase in frictional force. In some embodiments, when one of the wires 26, 28, 30, and 32 is pulled to turn the grasping portions 12*a* and 12*b*, the tension of the wires 26, 28, 30, and 32 is applied to the second rotating shaft 22 via the jaw pulleys 24. The force applied to the inner circumference of the through-hole of the support 14 for supporting the second rotating shaft 22 is then transmitted to the circular through-hole 14*a* in which the bearing 15 is mounted, and the support 14 is thus pressed toward the first rotating shaft 16. In this case as well, a normal force received by the support 14 from the first rotating shaft 16 is generated, which contributes to an increase in frictional force.

In the forceps device 10, however, the bearing is provided between the support 14 and the first rotating shaft 16, which reduces the frictional force between the first rotating shaft 16 and the support 14. Note that, when the bearing 15 is a rolling bearing, the frictional force between the first rotating shaft 16 and the support 14 can further be reduced. Consequently, the movement of the grasping portions 12*a* and 12*b* becomes smoother, and the controllability of the forceps device 10 improves. Note that the bearing may be a plain bearing. The bearing 15 may have a diameter of 3.6 to 4.5 mm, and the guide pulleys 20 may have a diameter of 3.0 to 3.6 mm. The bearing 15 may have a diameter larger than that of the guide pulleys 20.

[Grasping Portions]

Figure 9:
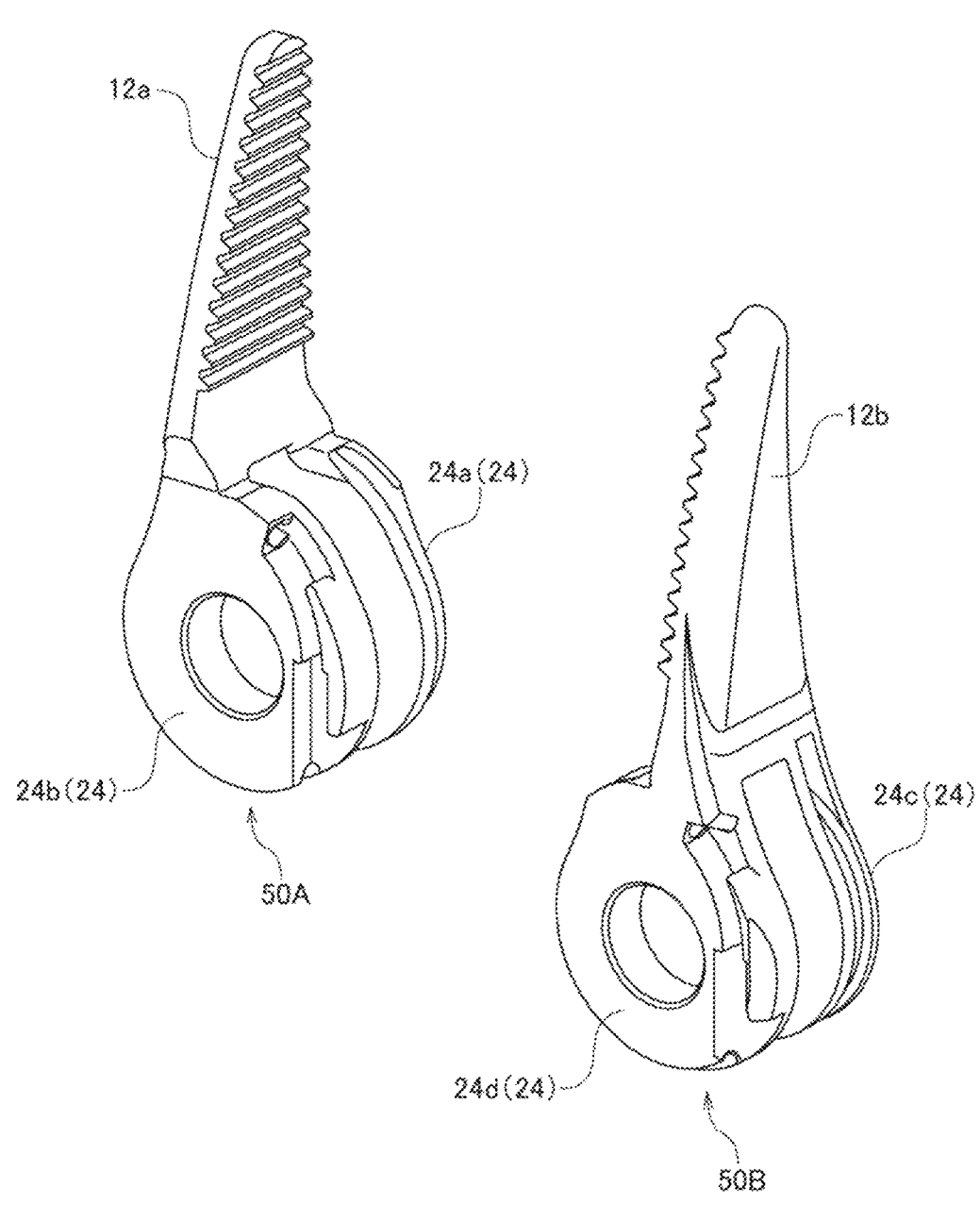
FIG. 9 is a perspective view illustrating a state in which a pair of jaw parts facing each other are to be fitted according to an embodiment.

Next, jaw parts constituting the grasping portions will be described in detail. FIG. 9 is a perspective view illustrating a state in which a pair of jaw parts facing each other are to be fitted. Jaw parts 50A and 50B illustrated in FIG. 9 are parts having substantially the same shapes as each other. The jaw parts 50A and 50B have the grasping portion 12*a* and the grasping portion 12*b*, respectively, which move relative to each other to grasp an object. The grasping portion 12*a* is continuous with a jaw pulley 24*a* (first grasping portion pulley) and a jaw pulley 24*b* (second grasping portion pulley), which are formed in a bifurcated shape, and the grasping portion 12*a* and the jaw pulleys 24*a* and 24*b* integrally constitute the jaw part 50A. In some embodiments, the grasping portion 12*b* is continuous with a jaw pulley 24*c* (third grasping portion pulley) and a jaw pulley 24*d* (fourth grasping portion pulley), which are formed in a bifurcated shape, and the grasping portion 12*b* and the jaw pulleys 24*c* and 24*d* integrally constitute the jaw part 50B.

Figure 10:
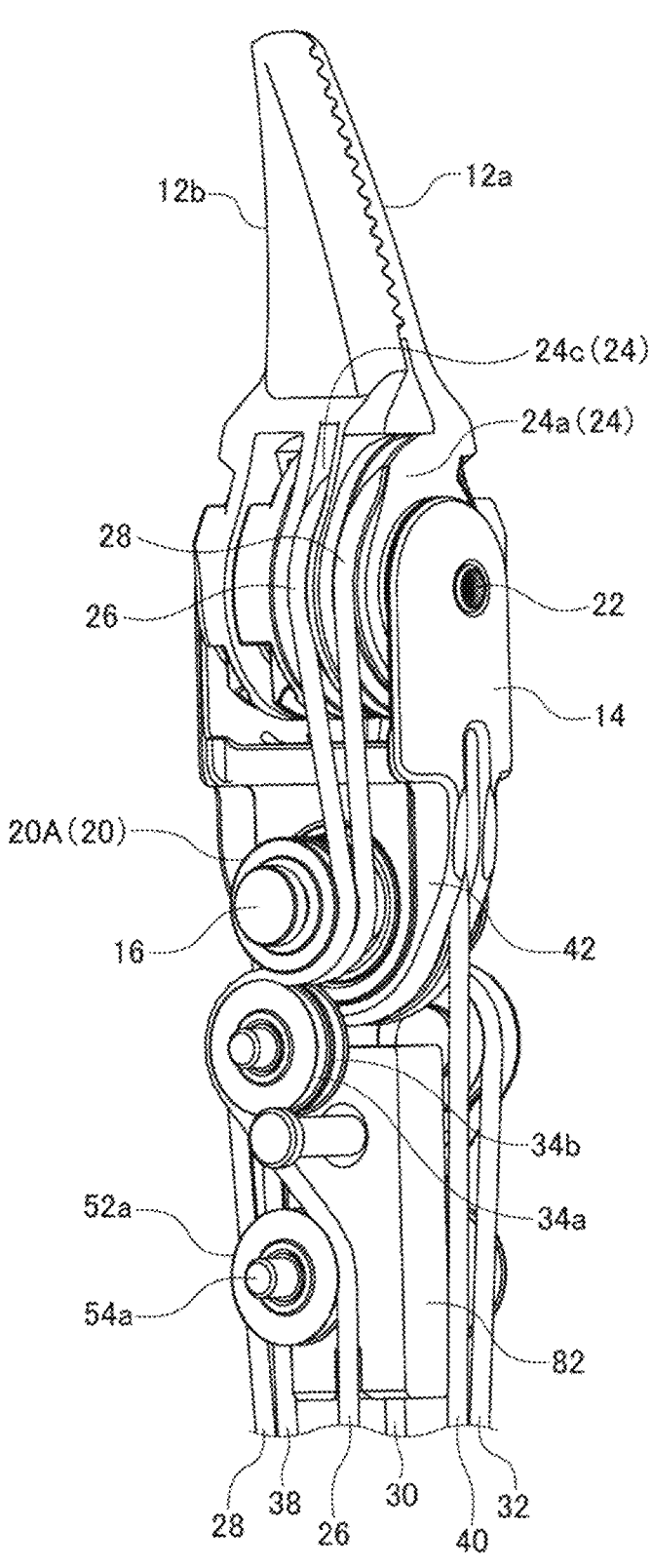
FIG. 10 is a perspective view of the forceps device illustrated in FIG. 1 as viewed in a direction H1.
Figure 11:
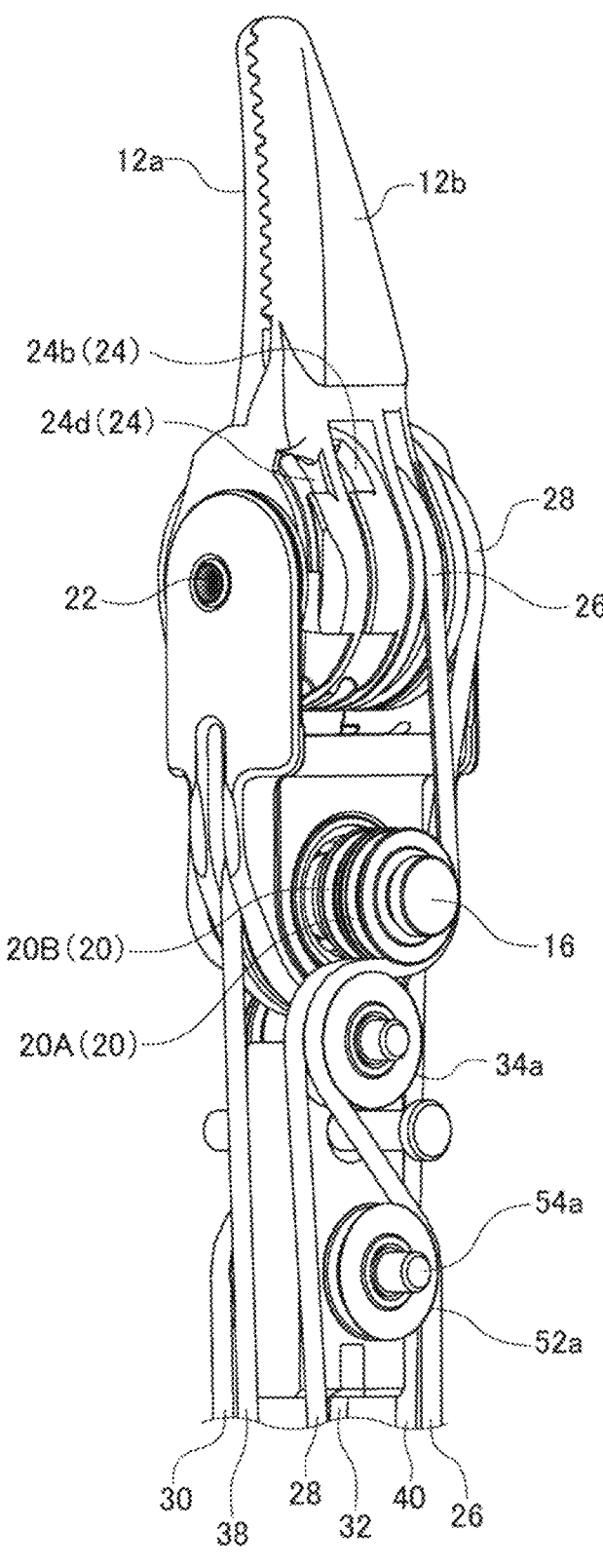
FIG. 11 is a perspective view of the forceps device illustrated in FIG. 1 as viewed in a direction H2.
Figure 12:
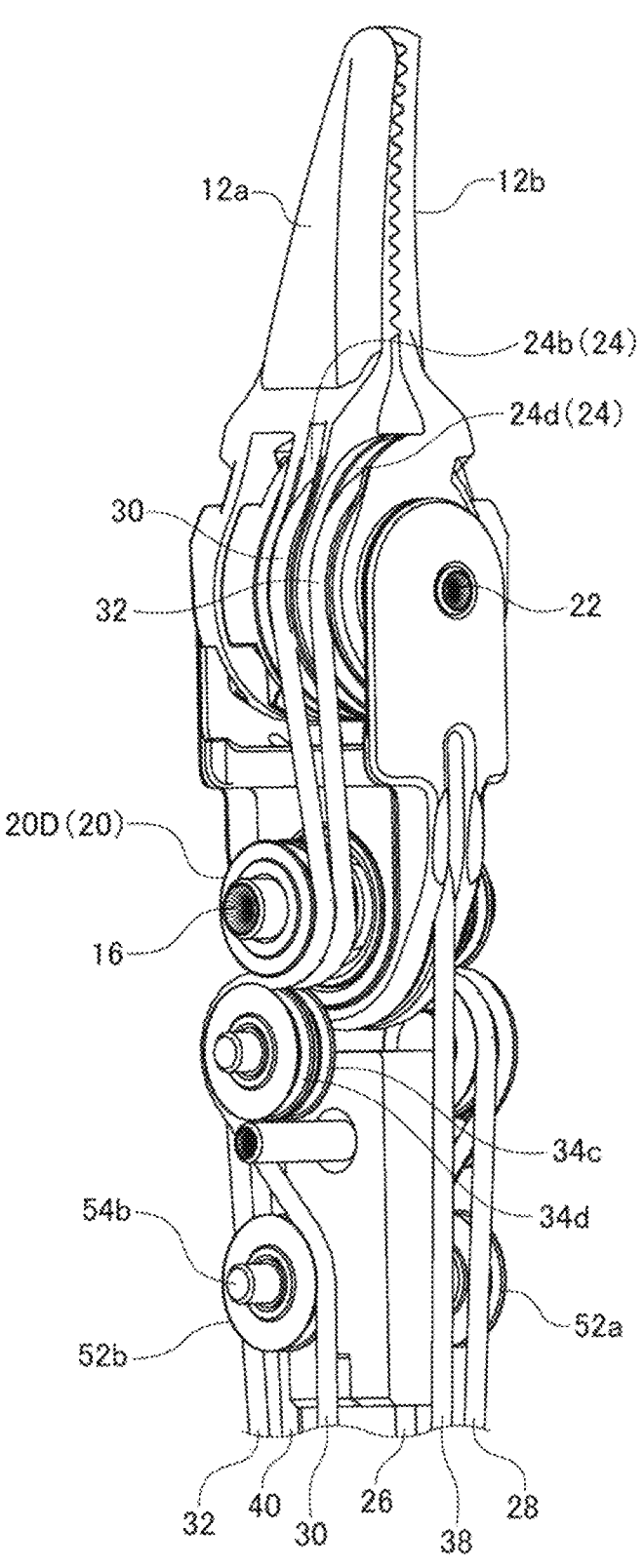
FIG. 12 is a perspective view of the forceps device illustrated in FIG. 1 as viewed in a direction H3.
Figure 13:
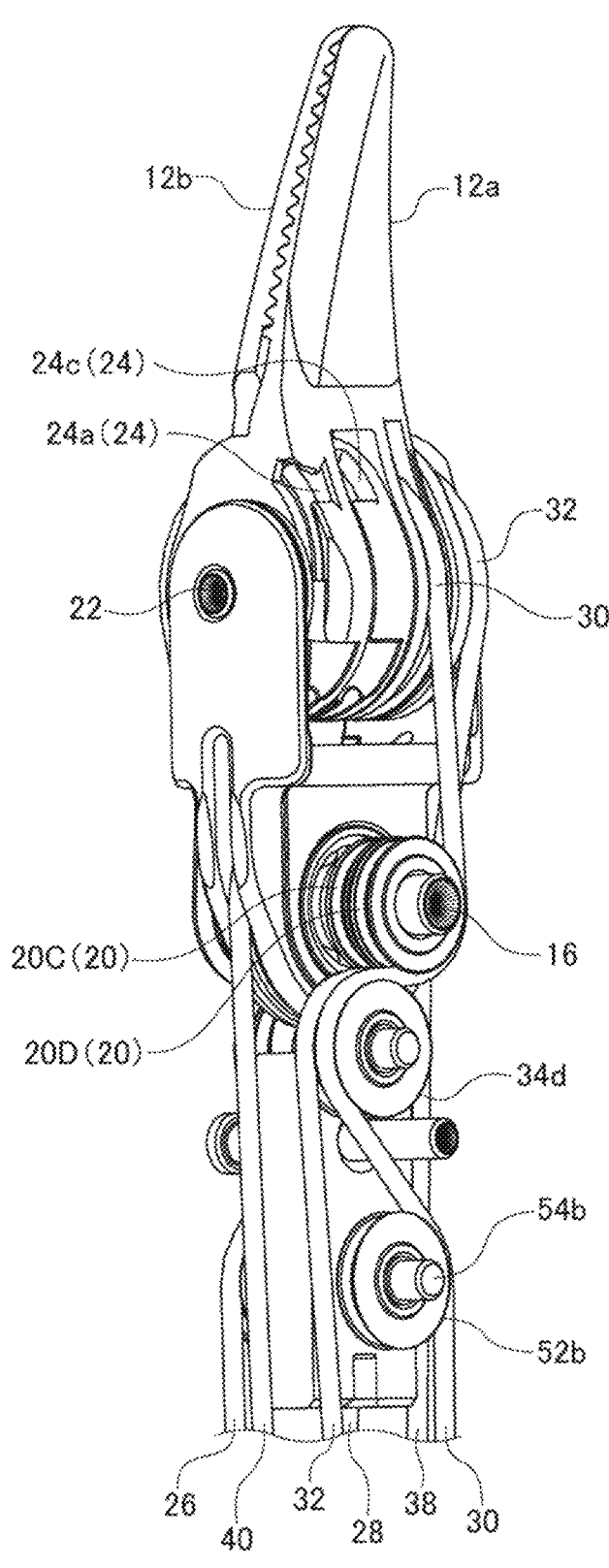
FIG. 13 is a perspective view of the forceps device illustrated in FIG. 1 as viewed in a direction opposite the direction H2.

FIG. 10 is a perspective view of the forceps device 10 illustrated in FIG. 1 as viewed in a direction H1. FIG. 11 is a perspective view of the forceps device 10 illustrated in FIG. 1 as viewed in a direction H2. FIG. 12 is a perspective view of the forceps device 10 illustrated in FIG. 1 as viewed in a direction H3. FIG. 13 is a perspective view of the forceps device 10 illustrated in FIG. 1 as viewed in a direction opposite the direction H2. Note that the directions H1 to H3 are directions within a horizontal plane H including the first rotating shaft 16. It is noted that the base member 18 is not illustrated in FIGS. 10 to 13.

As illustrated in FIGS. 10 to 13, the jaw pulley 24*a*, the jaw pulley 24*c*, the jaw pulley 24*b*, and the jaw pulley 24*d* are rotatably supported in this order by the second rotating shaft 22. In some embodiments, the guide pulley 20A, the guide pulley 20B, the guide pulley 20C, and the guide pulley 20D are rotatably supported in this order by the first rotating shaft 16. The wires 26, 28, 30 and 32, which are grasping-portion wires for transmitting driving forces for causing the grasping portions 12a and 12b to perform opening and closing movements, run between the guide pulleys 20A to 20D and the grasping portions 12a and 12b without other pulleys. Note that the driving forces are input from an actuator unit outside of the forceps device 10. This configuration can shorten the distance between the first rotating shaft 16 and the second rotating shaft 22 as illustrated in FIG. 10, etc., and can therefore increase the torque (operation force) of the grasping portions 12a and 12b. Consequently, the forceps device 10 with high controllability of the grasping portions 12a and 12b can be provided.

[How Wires Run Over Pulleys]

Next, the manner in which the wires 26, 28, 30 and 32 run over the pulleys will be described in detail. The wire 26 runs between the guide pulley 20A and the jaw pulley 24c. The wire 28 runs between the guide pulley 20B and the jaw pulley 24a. The wire 30 runs between the guide pulley 20D and the jaw pulley 24b. The wire 32 runs between the guide pulley 20C and the jaw pulley 24d.

Figure 14:
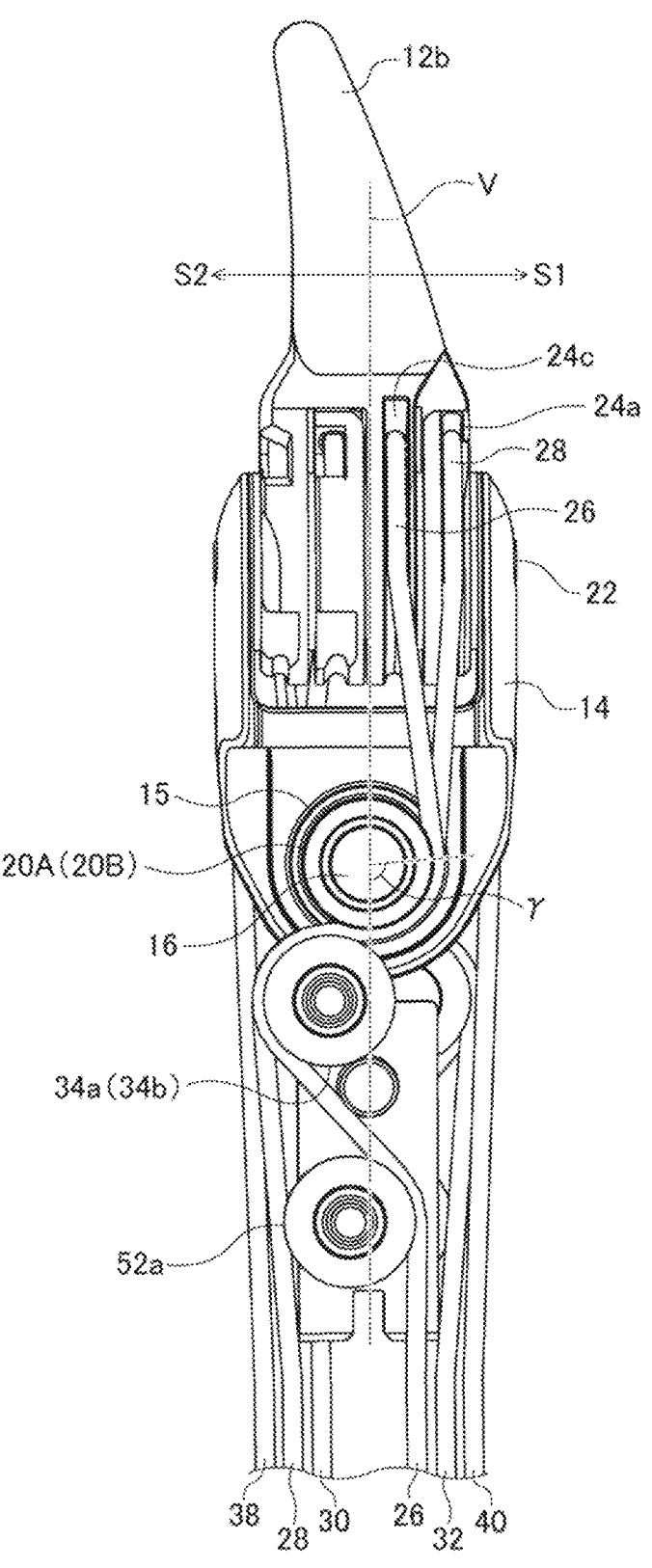
FIG. 14 is a schematic view of the forceps device illustrated in FIG. 3 omitting a base member, according to some embodiments.
Figure 15:
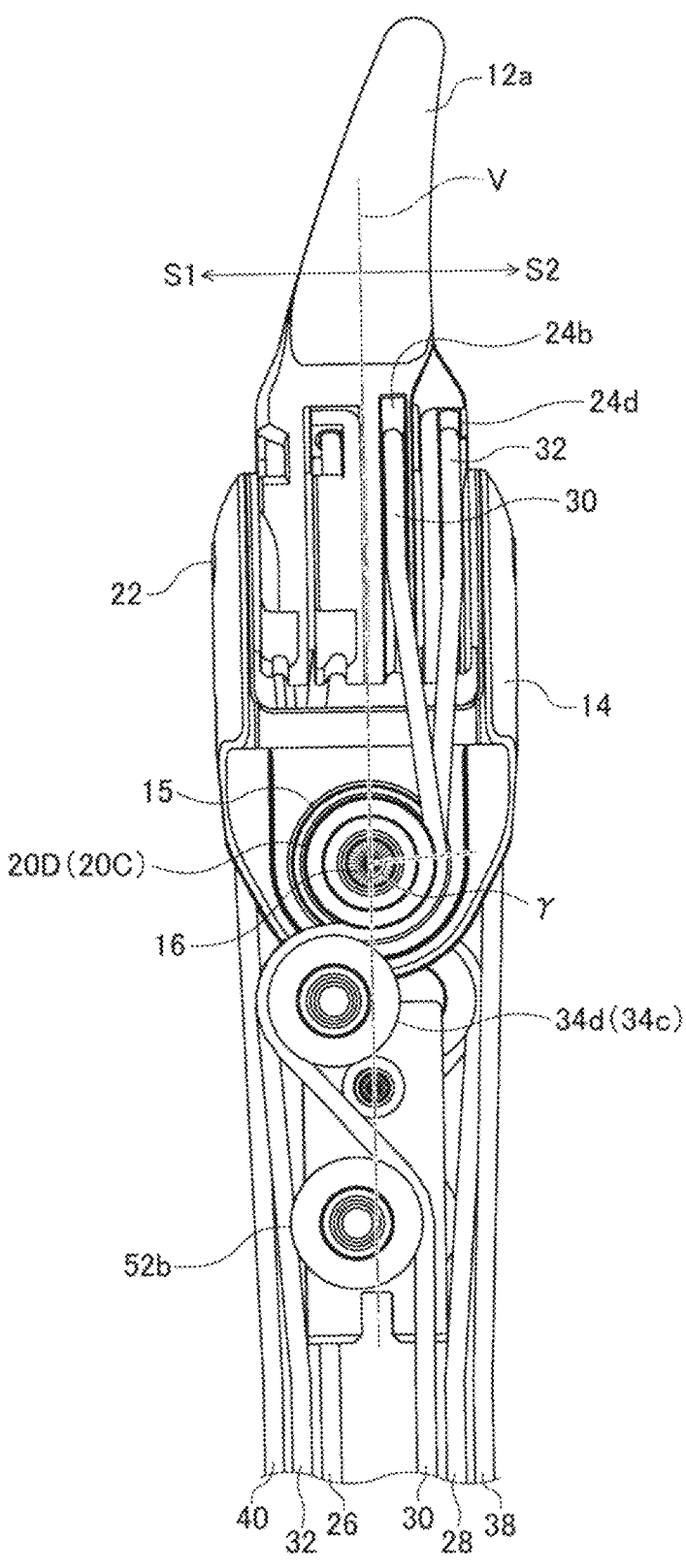
FIG. 15 is a schematic view of the forceps device illustrated in FIG. 4 omitting the base member, according to some embodiments.

FIG. 14 is a schematic view of the forceps device 10 illustrated in FIG. 3 omitting base member 18, according to some embodiments. FIG. 15 is a schematic view of the forceps device 10 illustrated in FIG. 4 omitting the base member, according to some embodiments.

As illustrated in FIGS. 10, 11, and 14, the wire 26 is passed over a first side S1 of the guide pulley 20A with respect to a vertical cross section V including the first rotating shaft 16 and being perpendicular to the second rotating shaft 22, and then fixed to the jaw pulley 24c located on the first side S1 with respect to the vertical cross section V. The wire 28 is passed over the first side S1 of the guide pulley 20B with respect to the vertical cross section V, and then fixed to the jaw pulley 24a located on the first side S1 with respect to the vertical cross section V.

In some embodiments, as illustrated in FIGS. 12, 13, and 15, the wire 30 is passed over the second side S2 of the guide pulley 20D with respect to the vertical cross section V, and then fixed to the jaw pulley 24b located on the second side with respect to the vertical cross section V. The wire 32 is passed over the second side S2 of the guide pulley 20C with respect to the vertical cross section V, and then fixed to the jaw pulley 24d located on the second side S2 with respect to the vertical cross section V. As a result, the four grasping-portion wires are fixed to the four grasping portion pulleys, respectively, without intersecting with each other.

In some embodiments, the forceps device 10 includes the guide pulley 34a on the upstream side of the guide pulley 20A (on the side opposite the grasping portions) and on the second side S2 with respect to the vertical cross section V, the guide pulley 34b on the upstream side of the guide pulley 20B and on the second side S2 with respect to the vertical cross section V, the guide pulley 34c on the upstream side of the guide pulley 20C and on the first side S1 with respect to the vertical cross section V, and the guide pulley 34d on the upstream side of the guide pulley 20D and on the first side S1 with respect to the vertical cross section V.

As a result, when the support 14 is bent in either direction about the first rotating shaft 16, one or more of the wires 26, 28, 30 and 32 come in contact with the associated one or more of the guide pulleys 20A to 20D, which stabilizes the controllability when the support 14 is turned. More specifically, when the support 14 is bent from the state illustrated in FIG. 14 toward the second side S2, the wires 26 and 28 come in contact with the guide pulleys 20A and 20B, respectively. In some embodiments, when the support 14 is bent from the state illustrated in FIG. 15 toward the first side S1, the wires 30 and 32 come in contact with the guide pulleys 20C and 20D, respectively. Thus, in either case, such a state in which none of the wires are in contact with the guide pulleys 20A to 20D (run over the guide pulleys 20A to 20D) is avoided. As a result, the controllability when the support 14 is bent about the first rotating shaft 16 is stabilized.

[Sealing of Base Member]

Because the grasping portions 12a and 12b of the forceps device 10 are operated inside the abdominal cavity of a patient, it is advantageous to devise a way to prevent gas around the grasping portions 12a and 12b from leaking out through the forceps device 10 so that the air pressure in the abdominal cavity, which is increased to be higher than the atmospheric pressure, does not lower. In some embodiments, sealing is therefore provided in a region including the base member 18.

Figure 16:
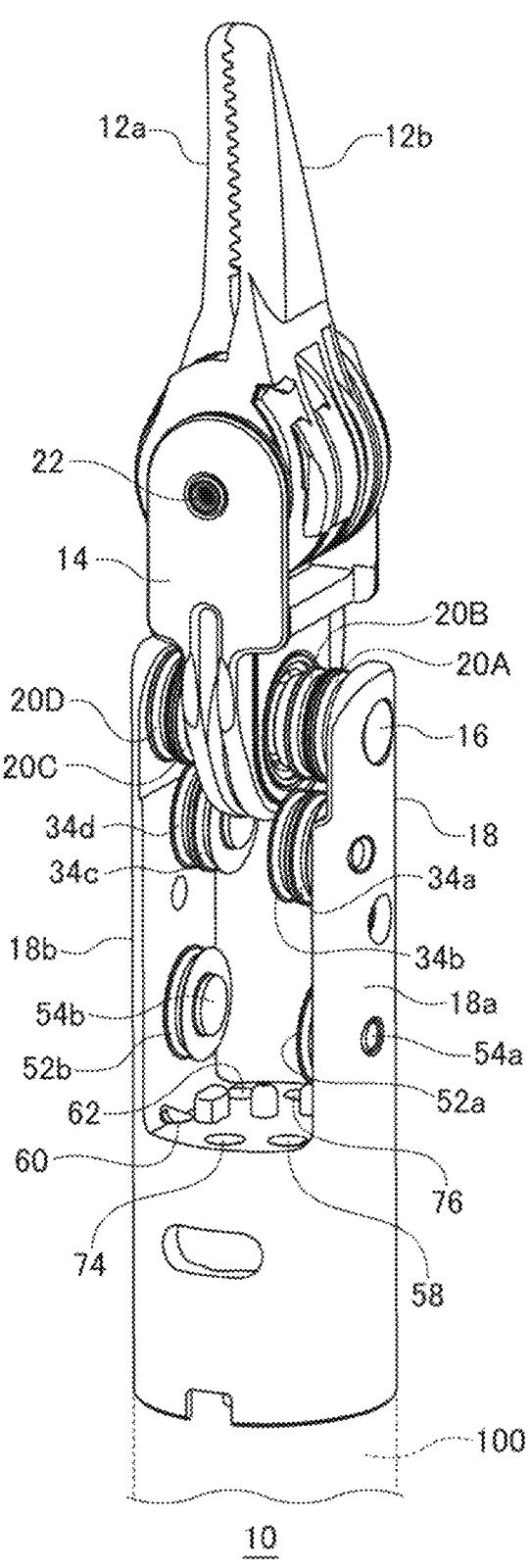
FIG. 16 is a schematic view of the forceps device illustrated in FIG. 1 omitting wires, according to some embodiments.

FIG. 16 is a schematic view of the forceps device illustrated in FIG. 1 omitting wires, according to some embodiments. As illustrated in FIG. 16, the forceps device 10 includes the pair of grasping portions 12a and 12b, the support 14 that holds the pair of grasping portions 12a and 12b, the first rotating shaft 16 that turnably supports the support 14, the base member 18 that holds the first rotating shaft 16, a plurality of wires 26, 28, 30 and 32 (not illustrated in FIG. 16; see FIG. 2) for transmitting driving forces to the pair of grasping portions 12a and 12b to move the grasping portions 12a and 12b, a guide pulley 52a for guiding the wire 26, a guide pulley 52b for guiding the wire 30, and support shafts 54a and 54b that rotatably support the guide pulleys 52a and 52b. The base member 18 is located between the grasping portions 12a and 12b and a shaft 100 of the forceps device 10.

Figure 17:
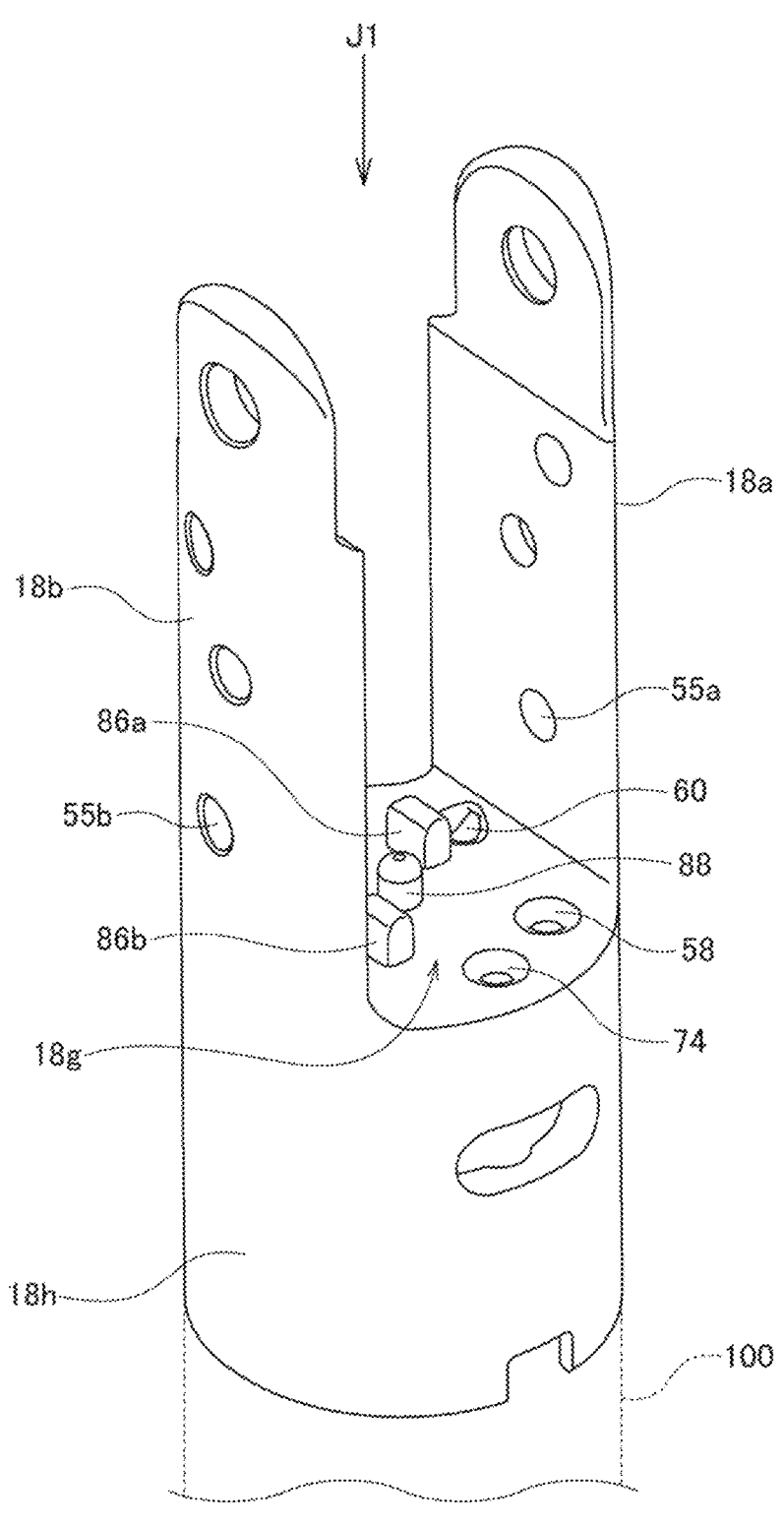
FIG. 17 is a perspective view of the base member according to an embodiment.
Figure 18:
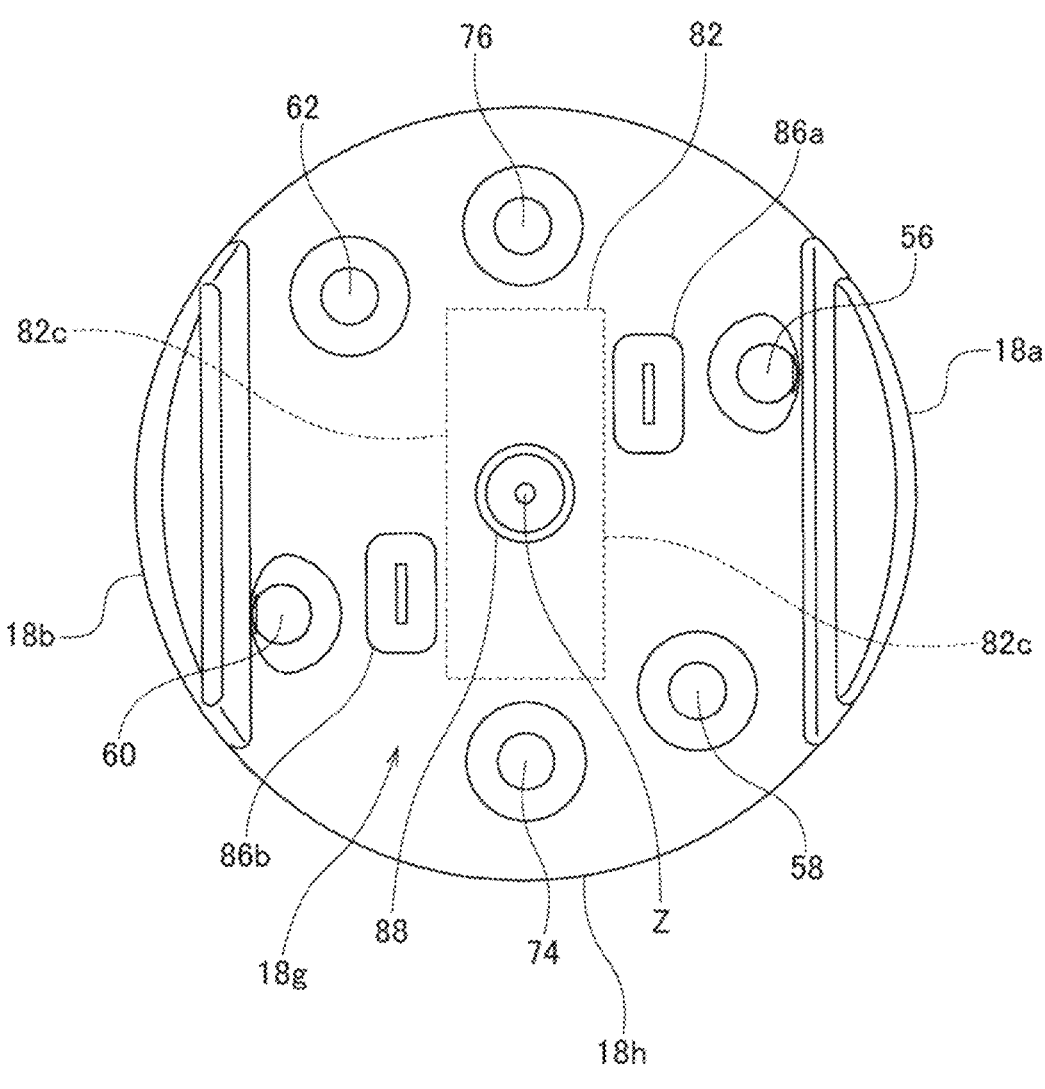
FIG. 18 is a top view of the base member illustrated in FIG. 17 as viewed in a direction J1.

FIG. 17 is a perspective view of the base member according to an embodiment. FIG. 18 is a top view of the base member illustrated in FIG. 17 as viewed in a direction J1.

The base member 18 includes a partition part 18g having a plurality of grasping-portion-wire holes 56, 58, 60 and 62 through which the wires 26, 28, 30 and 32, respectively, pass, and the pair of arms 18a and 18b which extend from an outer edge of the partition part 18g toward the grasping part (upward in FIG. 17) and to which the support shafts 54a and 54b are fixed. The arms 18a and 18b have fitting holes 55a and 55b, respectively, into which ends of the support shafts 54a and 54b that rotatably support the pair of guide pulleys 52a and 52b are fitted.

The partition part 18g is a partition formed between a cylindrical part 18h and the pair of arms 18a and 18b. The grasping-portion-wire holes 56 and 58 are a pair of grasping-portion-wire holes that are adjacent to each other at the closet distance, and the grasping-portion-wire holes 60 and 62 are a pair of grasping-portion-wire holes that are adjacent to each other at the closest distance.

As illustrated in FIG. 10, the wires 26 and 28 in a state being guided by the guide pulleys 34a and 34b are arranged together. Thus, for passing the wires 26 and 28 in this state through the partition part 18g, a large hole through which two wires can pass may be formed through the partition part 18g or two small holes through each of which one wire can pass may be formed through the partition part 18g. In the case of a large hole, the airtightness of sealing with sealing resin, which will be described later, may be lowered. In contrast, in the case of two adjacent small holes, the wall between the holes becomes thin, and the strength of an area of the base member 18 where the holes are formed may therefore be lowered.

Hence, in the forceps device 10, the wire 26 is guided by the guide pulley 52a, so that the wire 26 is separated from the wire 28. Similarly, the wire 30 is guided by the guide pulley 52b, so that the wire 30 is separated from the wire 32. In this manner, the grasping-portion-wire hole 56 through which the wire 26 passes and the grasping-portion-wire hole 58 through which the wire 28 passes can be separated from each other. Similarly, the grasping-portion-wire hole 60 through which the wire 30 passes and the grasping-portion-wire hole 62 through which the wire 32 passes can be separated from each other.

In some embodiments, the base member 18 includes an elastic sealing member (having a type A durometer hardness of 30 to 70) arranged on one side (on one side opposite the side in which the grasping portions 12a and 12b are located) with respect to the partition part 18g. The sealing member is a silicone resin film having a thickness of about 0.5 to 2 mm, for example.

The sealing member has a plurality of sealing holes at positions corresponding to those of the grasping-portion-wire holes 56, 58, 60 and 62. This configuration enables sealing with the sealing member, with the wires 26, 28, 30 and 32 passing through the partition part 18g of the base member 18. The wires have a diameter φ of 0.4 to 0.5 mm, and the diameter of the grasping-portion-wire holes is preferably slightly larger than the wire diameter.

The sealing holes have a diameter that is smaller than diameter of the grasping-portion-wire holes and smaller than the diameter (wire diameter q) of the grasping-portion wires. As a result, even when a gap is present between a grasping-portion-wire hole and a grasping-portion wire, the sealing hole and the grasping-portion wire are in close contact with each other, which reduces leakage of gas from the grasping part side to the outside of the forceps device 10 via the base member 18.

As illustrated in the drawings, the four grasping-portion-wire holes may be formed through the partition part 18g at certain distances from each other. Thus, the sealing holes formed at positions corresponding to those of the grasping-portion-wire holes are also separated from the adjacent sealing holes.

In some embodiments, the forceps device 10 includes the pair of wires 38 and 40 for turning the support 14 about the first rotating shaft 16 In some embodiments to the wires 26, 28, 30 and 32, which are grasping-portion wires. The partition part 18g of the base member 18 therefore has support-wire holes 74 and 76 through which the wires 38 and 40, respectively, pass. The support-wire holes 74 and 76 are formed at point-symmetric positions with respect to the center Z of the partition part 18g (the central axis of the cylindrical part 18h).

In some embodiments, the sealing member has a plurality of sealing holes formed at positions corresponding to those of the support-wire holes 74 and 76. This enables sealing with the sealing member, with the wires 38 and 40 passing through the partition part 18g of the base member 18. The diameter of the support-wire holes is preferably slightly larger than the wire diameter. In some embodiments, the arrangement of the pulleys of the forceps device 10 is devised so that a plurality of holes for wires formed in the partition part 18g of the base member 18 can be suitably separated from each other. This configuration reduces such a problem as unintended integration of holes for wires in forming the sealing member having a plurality of holes for wires.

[Turning Restricting Mechanism]

In the forceps device 10 illustrated in FIG. 2, in a state in which the driving force for turning the support 14 is transmitted via the wires 38 and 40, the grasping portions 12a and 12b are bent at an angle in a control range (±80° in the embodiment) that prevents part of the support 14 and the grasping-portion wires 26, 28, 30, and 32 from interfering with each other. In a state in which the forceps device 10 is detached from a power source or a main unit of a robot, however, the support 14 is freely turnable beyond the angles in the control range, and a partial region R of the support illustrated in FIG. 2 may therefore touch the grasping-portion wires 26, 28, 30, and 32.

Thus, the forceps device 10 includes a turning restricting mechanism for restricting turning of the support to prevent the turning support 14 from touching the grasping-portion wires 26, 28, 30, and 32. The turning restricting mechanism includes a stopper having a face with which part of the turning support comes into contact.

Figure 19:
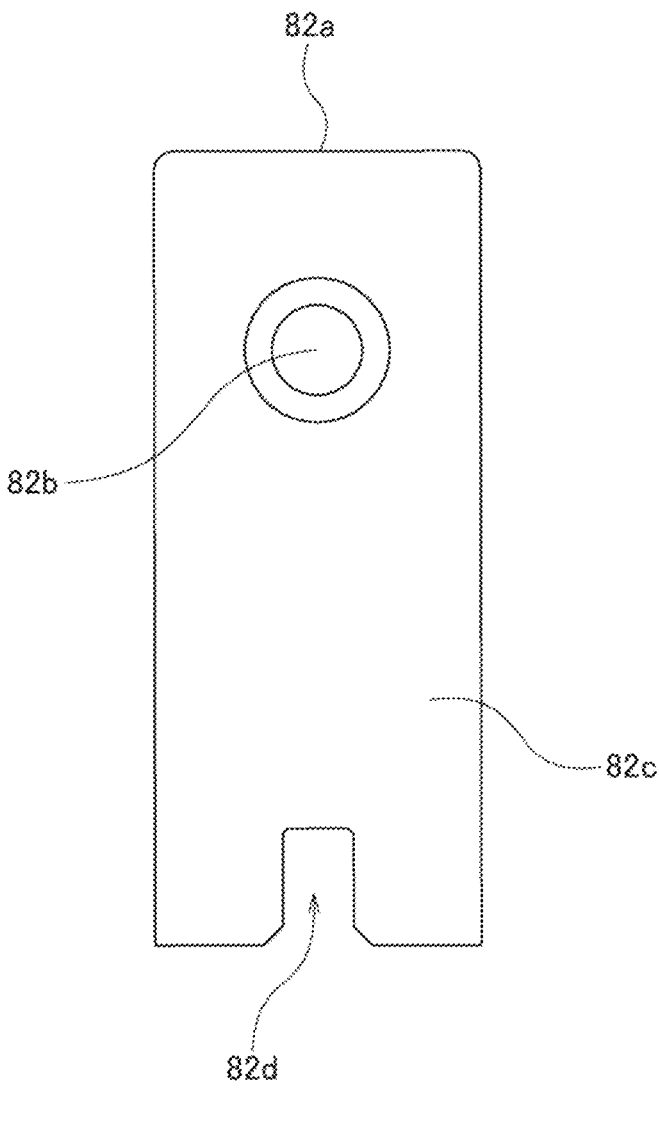
FIG. 19 is a front view of a stopper according to an embodiment.
Figure 20:
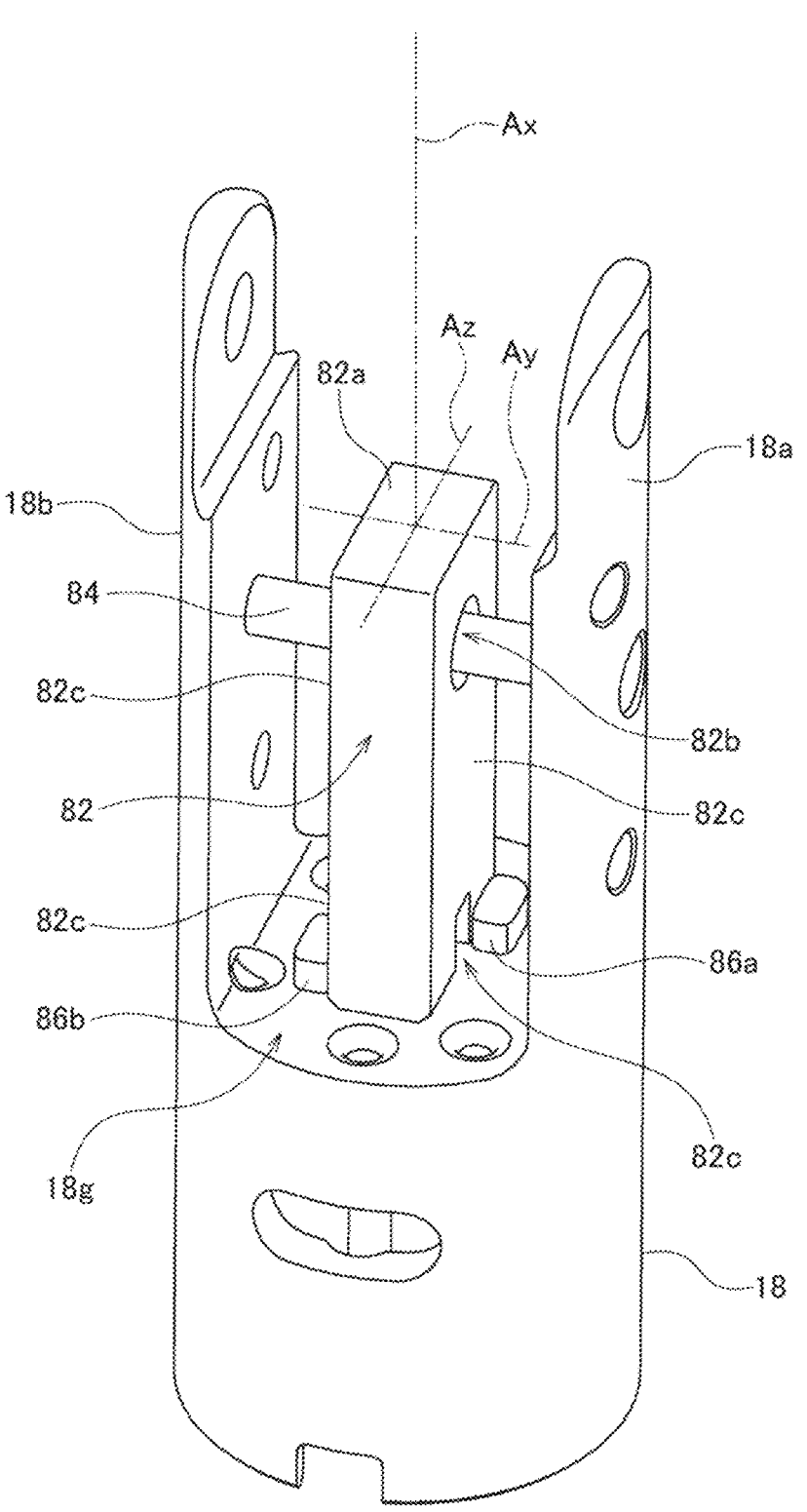
FIG. 20 is a drawing for explaining the stopper positioned in the base member, according to an embodiment.

FIG. 19 is a front view of the stopper according to an embodiment. FIG. 20 is a drawing for explaining the stopper positioned in the base member 18, according to an embodiment.

The stopper 82 is a block-like rectangular parallelepiped member having a flat face 82a, which faces the support 14, serving as the face with which the turning support comes into contact. When a contact face 14b of the support 14 comes into contact with the flat face 82a (see FIGS. 2 and 7 to 9), further turning of the support 14 is restricted. In this manner, the turning restricting mechanism is achieved with a simple part. Furthermore, because the support 14 is prevented from touching the grasping-portion wires 26, 28, 30, and 32, the durability of the grasping-portion wires is improved, and therefore the product life of the forceps device 10 is extended.

As described above, because the support 14 and the stopper 82 directly come in contact with each other, the turning restricting mechanism can more reliably prevent contact between the support and the grasping-portion wires.

In some embodiments, as illustrated in FIG. 7, the contact face 14b formed at an outer edge of the support 14 is a flat surface inclined with respect to the central axis Ax (the axis passing the center Z shown in FIG. 18) of the base member 18 at the neutral position (the state illustrated in FIG. 3, for example) at which the support 14 is not turned to the left or to the right. The support 14 is designed to come into contact with the stopper 82 when the turning angle from the neutral position becomes a contact angle β (α<β) beyond the angles α in the predetermined control range. This configuration and operation prevents the support 14 from turning at angles larger than the contact angle β while permitting turning at the angles α in the predetermined control range, which prevents hindrance to turning control of the support 14 by the stopper 82.

Note that, in some embodiments, the contact angle β may be 70° or larger. In some embodiments, the contact angle β may be larger than 90°. This configuration enables control of the turning of the support at least up to 70°. If the contact angle β is too large, however, the support 14 may touch the grasping-portion wires before the support 14 comes into contact with the stopper 82. In an embodiment, the contact angle β may be therefore smaller than a turning angle at which the support 14 touches a grasping-portion wire.

Specifically, in an embodiment, the contact angle β may be smaller than 110°. In some embodiments, the contact angle β may be smaller than 100°.

Note that, if the contact angle β varies, the support 14 may unintentionally touch a grasping-portion wire. Positioning of the stopper 82 is therefore important. The stopper 82 is positioned relative to the base member 18. As a result, both the support 14 and the stopper 82 are at predetermined positions relative to the base member 18, which improves the accuracy of relative positions of the support 14 and the stopper 82.

Specific positioning in the embodiment will be explained. As illustrated in FIG. 19, a through-hole 82b is formed in a side face of the stopper 82. In some embodiments, as illustrated in FIG. 20, the pair of arms 18a and 18b of the base member 18 holds a positioning pin 84 that is inserted in and extending through the through-hole 82b of the stopper 82. Thus, the stopper 82 can be accurately positioned in the direction of the central axis Ax of the base member 18. Furthermore, because the pair of arms 18a and 18b holds the positioning pin 84, the strength of the arms is increased.

In some embodiments, the partition part 18g at the base part of the arms 18a and 18b of the base member 18 has a plurality of projections 86a, 86b, and 88 used for positioning of the stopper 82. The shapes and the arrangement of the projections 86a and 86b are set for positioning in a direction Ay intersecting the central axis Ax when the projections 86a and 86b come in contact with a pair of side faces 82c, which are opposite each other, of the stopper 82. In some embodiments, the shape and the arrangement of the projection 88 are set for positioning in a direction Az intersecting the central axis Ax and the direction Ay when the projection 88 is fitted into a groove 82d formed at a lower portion of the stopper 82. Thus, the stopper 82 can be accurately positioned in the directions Ay and Az intersecting the axial direction Ax of the base member 18.

In some embodiments, as illustrated in FIGS. 10 and 18, the stopper 82 is arranged in a region surrounded by a plurality of grasping-portion wires and support wires. Thus, the region surrounded by the plurality of wires is occupied by the stopper 82, which prevents foreign substances from staying inside the forceps device 10 (in a region surrounded by the wires) as compared with a case where no stopper is provided.

[Arrangement of Pulleys]

In the forceps device 10, the arrangement of the pulleys is devised so as to improve the durability of the wires while allowing some degree of wire winding angle. Specifically, as illustrated in FIG. 14, the guide pulleys 34a and 34b are shifted toward one side (toward S2) relative to immediately below the guide pulleys 20A and 20B when the first rotating shaft 16 is viewed in front in the axial direction in a state in which the leading ends of the grasping portions 12a and 12b point upward. Furthermore, the guide pulleys 34a and 34b are arranged so that the winding angle γ of the grasping-portion wires 26 and 28 around the guide pulleys 20A and 20B is 65° or larger at the neutral position at which the support 14 is not turned to the left or to the right.

This configuration enables comfortable operation control with the turning angle of the support 14, which holds the grasping portions 12a and 12b, being at least within a range of ±65°. Note that the winding angle γ may be 89° or larger. This configuration enables comfortable operation control with the turning angle of the support, which holds the grasping portions 12a and 12b, being at least within a range of ±89°.

The guide pulley 52a is located upstream of the guide pulleys 34a and 34b, and the grasping-portion wire 26 runs over the guide pulley 52a. The guide pulley 52a is shifted toward one side (toward S2) relative to immediately below the guide pulleys 20A and 20B and shifted toward the other side (toward S1) relative to immediately below the guide pulleys 34a and 34b when the first rotating shaft 16 is viewed in front in the axial direction in the state in which the leading ends of the grasping portions 12a and 12b point upward. This configuration increases the radius of curvature of an S-shaped curve of the grasping-portion wire 26 running over the guide pulley 34a and the guide pulley 52a. Furthermore, as a result of the increase in the radius of curvature of the S-shaped curve of the grasping-portion wire 26, bending stress generated in the grasping-portion wire 26 is lowered, and the durability of the grasping-portion wires relating to opening and closing movements of the grasping portions 12a and 12b is improved.

Similarly, as illustrated in FIG. 15, the guide pulleys 34d and 34c is shifted toward one side (toward S1) relative to immediately below the guide pulleys 20D and 20C when the first rotating shaft 16 is viewed in front in the axial direction in the state in which the leading ends of the grasping portions 12a and 12b point upward. In some embodiments, the guide pulleys 34d and 34c are arranged so that the winding angle γ of the grasping-portion wires 30 and 32 around the guide pulleys 20D and 20C is 65° or larger at the neutral position at which the support 14 is not turned to the left or to the right.

The guide pulley 52b is located upstream of the guide pulleys 34d and 34c, and the grasping-portion wire 30 runs over the guide pulley 52b. The guide pulley 52b is shifted toward one side (toward S1) relative to immediately below the guide pulleys 20D and 20C and shifted toward the other side (toward S2) relative to immediately below the guide pulleys 34d and 34c when the first rotating shaft 16 is viewed in front in the axial direction in the state in which the leading ends of the grasping portions 12a and 12b point upward. This configuration increases the radius of curvature of an S-shaped curve of the grasping-portion wire 30 running over the guide pulley 34d and the guide pulley 52b. Furthermore, as a result of the increase in the radius of curvature of the S-shaped curve of the grasping-portion wire 30, bending stress generated in the grasping-portion wire 30 is lowered, and the durability of the grasping-portion wires relating to opening and closing movements of the grasping portions 12a and 12b is improved.

Note that, as illustrated in FIG. 16, the guide pulleys 52a and 52b are located on respective sides of the inner wall of the base member 18. The guide pulleys 52a and 52b are also rotatably supported by different support shafts 54a and 54b, respectively, which are held by the base member 18. This configuration enables the guide pulley 52a and the guide pulleys 34a and 34b to be arranged on the same side (right side in FIG. 16) when the guide pulley 20A is viewed from the front. Similarly, the guide pulley 52b and the guide pulleys 34c and 34d can be arranged on the same side (left side in the embodiment) when the guide pulley 20D is viewed from the front.

Note that the base member 18 is a cylindrical part having an outer diameter of 7 to 9 mm. Furthermore, the guide pulleys 20A to 20D have a diameter of 3.0 to 3.6 mm, the guide pulleys 34a to 34d have a diameter of 3.0 to 3.6 mm, and the guide pulleys 52a and 52b have a diameter of 3.0 to 3.6 mm. As a result, in a forceps device having a very small outer diameter, the radius of curvature of each S-shaped curve can be increased while appropriate winding angles are achieved.

While various embodiments have been described above with reference to the drawings, the various embodiments are not limited to the description above, and any combination or substitution of components as appropriate is included in the scope of the appended claims. In addition, modifications such as combinations, changes in the order of processes, and various changes in design may be made on an embodiment on the basis of knowledge of a person skilled in the art, and such modified embodiments may be within the scope of the appended claims.

What is claimed is:

1. A forceps device comprising:
a grasping part;
a support that holds the grasping part;
a first rotating shaft that turnably supports the support;
a base member that holds the first rotating shaft;
a plurality of grasping-portion wires that transmit driving forces to move the grasping part;
a support wire that transmits a driving force to turn the support about the first rotating shaft; and
a turning restricting mechanism that restricts turning of the support so that the support that is turned does not touch the plurality of grasping-portion wires.

2. The forceps device according to claim 1, wherein the turning restricting mechanism includes a stopper having a first face with which part of the support that is turned comes into contact.

3. The forceps device according to claim 2, wherein the stopper is a block member having a flat face that faces the support, the flat face serving as the first face.

4. The forceps device according to claim 3, wherein:
the support has an outer edge at which a flat contact face is formed, the flat contact face being inclined with respect to a central axis of the base member at a neutral position at which the support is not turned to left or right, the support coming into contact with the stopper when a turning angle from the neutral position becomes a contact angle β beyond angles α in a control range angle, and
wherein α<β.

5. The forceps device according to claim 4, wherein the contact angle β is 70° or larger.

6. The forceps device according to claim 2, wherein:
the support has an outer edge at which a flat contact face is formed, the flat contact face being inclined with respect to a central axis of the base member at a neutral position at which the support is not turned to left or right, the support coming into contact with the stopper when a turning angle from the neutral position becomes a contact angle β beyond angles α in a control range angle, and
wherein α<β.

7. The forceps device according to claim 6, wherein the contact angle β is 70° or larger.

8. The forceps device according to claim 2, wherein the stopper is positioned relative to the base member.

9. The forceps device according to claim 2, wherein the stopper is located in a region surrounded by the support wire and the plurality of grasping-portion wires.

10. The forceps device according to claim 2, wherein:
the base member includes a pair of arms that hold respective ends of the first rotating shaft, and
the pair of arms holds a positioning pin extending through the stopper.

11. The base member according to claim 10, wherein:
the base member includes a partition part at a base part of the pair of arms,
the partition part has a plurality of projections for positioning of the stopper, and
the plurality of projections are configured to position the stopper in a direction intersecting a central axis of the base member.

12. A forceps device comprising:
a grasping part;
a support that holds the grasping part;
a first rotating shaft that turnably supports the support;
a base member that holds the first rotating shaft;
a plurality of grasping-portion wires that transmit driving forces to move the grasping part;
a plurality of support wires that transmit a driving force to turn the support about the first rotating shaft; and
a stopper that prevents the support from touching the plurality of grasping-portion wires.

13. The forceps device according to claim 12, wherein the stopper is a block having a flat face that faces the support and with which part of the support comes into contact.

14. The forceps device according to claim 13, wherein:
the support has an outer edge at which a flat contact face is formed, the flat contact face being inclined with respect to a central axis of the base member at a neutral position at which the support is not turned to left or right, and
the support comes into contact with the stopper when a turning angle from the neutral position becomes a contact angle β.

15. The forceps device according to claim 14, wherein the contact angle β is 70° or larger.

16. The forceps device according to claim 12, wherein:
the support has an outer edge at which a flat contact face is formed, the flat contact face being inclined with respect to a central axis of the base member at a neutral position at which the support is not turned to left or right,
the support comes into contact with the stopper when a turning angle from the neutral position becomes a contact angle β, and
the contact angle β is 70° or larger.

17. The forceps device according to claim 12, wherein the stopper is located in a region surrounded by the plurality of grasping-portion wires and the plurality of support wires.

18. The forceps device according to claim 12, wherein:
the base member includes a pair of arms that hold respective ends of the first rotating shaft, and
the pair of arms holds a positioning pin extending through the stopper.

19. The base member according to claim 18, wherein:
the base member includes a partition part at a base part of the pair of arms,
the partition part has a plurality of projections for positioning of the stopper, and
the plurality of projections are configured to position the stopper in a direction intersecting a central axis of the base member.

20. A forceps device comprising:
a plurality of grasping portions;
a support that holds the plurality of grasping portions;
a first rotating shaft that turnably supports the support;
a base member that holds the first rotating shaft;
a plurality of first wires that transmit driving forces to move the plurality of grasping portions;

a plurality of second wires that transmit a driving force to
  turn the support about the first rotating shaft; and
a stopper that prevents the support from touching the
  plurality of first wires.

* * * * *